United States Patent
Weller et al.

(10) Patent No.: US 7,135,324 B2
(45) Date of Patent: Nov. 14, 2006

(54) VIRAL RECOMBINASES, RELATED ARTICLES, AND METHODS OF USE THEREOF

(75) Inventors: Sandra Weller, Unionville, CT (US); Richard S. Myers, Miami, FL (US); Nina Bacher Reuven, Bloomfield, CT (US)

(73) Assignee: The University of Connecticut, Storrs, CT (US)

( * ) Notice: Subject to any disclaimer, the term of this patent is extended or adjusted under 35 U.S.C. 154(b) by 178 days.

(21) Appl. No.: 10/656,868

(22) Filed: Sep. 4, 2003

(65) Prior Publication Data
US 2004/0141994 A1 Jul. 22, 2004

Related U.S. Application Data

(60) Provisional application No. 60/408,092, filed on Sep. 4, 2002.

(51) Int. Cl.
*C12N 9/22* (2006.01)
*C12N 15/10* (2006.01)
*A61K 38/46* (2006.01)

(52) U.S. Cl. .................. 435/199; 435/496; 424/946

(58) Field of Classification Search ............... 435/199, 435/490; 530/350; 424/94, 6; 514/12
See application file for complete search history.

(56) References Cited

U.S. PATENT DOCUMENTS

6,136,538 A * 10/2000 Olivo et al. .................. 435/6

FOREIGN PATENT DOCUMENTS

| EP | 0 225 189 B1 | 10/1992 |
|---|---|---|
| EP | 0 524 968 B1 | 6/1995 |
| EP | 0 465 529 B1 | 4/1998 |
| EP | 0 827 545 B1 | 2/2002 |
| WO | WO 91/16024 | 10/1991 |
| WO | WO 91/16116 | 10/1991 |
| WO | WO 91/17424 | 11/1991 |
| WO | WO 95/13796 | 5/1995 |

OTHER PUBLICATIONS

Reuven, N.B., et al. (2003) J. Virol. 77(13), 7425-7433.*
Reuven, N.B., et al. (2004) J. Virol. 78(9), 4599-4608.*
Friedman, et al., (2001), "Bacteriophage lambda: alive and well and still doing its thing" *Curr Opin Microbiol*; vol. 4, 201-207.
Goldstein, et al., (1998), The Exonuclease Activity of HSV-1 UL12 is Required for *in Vivo* Function; *Virology*, vol. 244, 442-457.
Gordon, Jon W., (1989), "Transgenic Animals"; *International Review of Cytology*, vol. 115, 171-229.
Haensler et al., (1993), "Synthesis and Characterization of a Trigalactosylated Bisacridine Compound To Target DNA to Hepatocytes"; *Bioconjugate Chem*, vol. 4, 85-93.
Hill, et al., (2000); "BAC Trimming: Minimizing Clone Overlaps", *Genomics*, vol. 64, 111-113.
Ikari et al., (2001); "α1-Proteinase Inhibitor, α1-Antichymotrypsin, and α2-Macroglobulin Are the Antiapoptotic Factors of Vacsular Smooth Muscle Cells", *Journal of Biological Chemistry*, vol. 276, No. 15, 11798-11803.
Ioffe et al., (1995); "WW6: An embryonic stem cell line with an inert genetic marker that can be traced in chimerax"; *Proc. Natl. Acad. Sci.*, vol. 92, 7357-7361.
Karlin, et al., (1990); "Methods for assessing the statistical significance of molecular sequence features by using general scoring schemes"; *Proc. Natl. Acad. Sci., U.S.A.*, vol. 87, 2264-2268.
Lavitrano et al., (1989); "Sperm Cells as Vectors for Introducing Foreign DNA into Eggs; Genetic Transformation of Mice"; *Cell*, vol. 57, 717-723.
Ledley, et al., (1991); "Clinical Considerations in the Design of Protocols for Somatic Gene Therapy"; *Human Gene Therapy*, vol. 2, 77-83.
Ledley, et al., (1996); "Pharmaceutical Approach to Somatic Gene Therapy"; *Pharmaceutical Research*, vol. 13, 1595-1613.
Lee, et al., (2001); "A Highly Efficient *Escherichia coli*-Based Chromosome Engineering System Adapted for Recombinogenic Targeting and Subcloning of BAC DNA"; *Genomics*, vol. 73, 56-65.
Legan et al, (1975); "Role of Estrogen as Initiator of Daily LH Surgers in the Ovariectomized Rat [1,2]"; *Endo*; vol. 96, 50-56.
Lo (1983); "Transformation by Iontophoretic Microinjectionof DNA: Multiple Integrations Without Tandem Insertions"; *Mol. Cell Biol.*, vol. 3, No. 10, 1803-1814.
Logan, et al., (1984); "Adenovirus tripartite leader sequence enhances transltion of nRNAs late after infection"; *Proc. Natl. Acad. Sci. U.S.A.*, vol. 81, 3655-3659.
Lowy, et al., (1980); "Isolation of Transforming DNA: Cloning the Hamster aprt Gene"; *Cell*, vol. 22, 817-823.

(Continued)

*Primary Examiner*—Charles L. Patterson, Jr.
(74) *Attorney, Agent, or Firm*—Cantor Colburn LLP

(57) ABSTRACT

A Herpes simplex virus (HSV) recombinase comprises a purified or isolated alkaline nuclease and a single stranded DNA binding protein. In HSV-1, the alkaline nuclease is the UL12 protein and the single stranded DNA binding protein is the ICP8 protein. The HSV recombinase can be purified from an in vitro expression system or can be expressed in an appropriate vector or vectors wherein the DNAs encoding the polypeptides are operatively linked to expression control sequences. Methods of use of the HSV recombinase include cloning, treating cells and organisms, and producing transgenic animals. The HSV recombinase can be in the form of a kit useful for cloning.

22 Claims, 6 Drawing Sheets

OTHER PUBLICATIONS

Muyrers, et al., (2000); "RecE/RecT and Redα/Redβ initiate double-stranded break repair by specifically interacting with their respective partners"; *Genes & Dev.*, vol. 14, 1971-1982.

Muyrers, et al., (2000); "Point mutation of bacterial artificial chromosomes by ET recombination"; *EMBO Rep.*, vol. 1, 239-243.

Muyrers, et al., (2000); "ET-Cloninbg: Think Recombination First"; *Genetic Eng*, vol. 22, 77-98.

Muyrers, et al., (1999); "Rapid modification of bacterial artificial chromosomes by ET-recombination"; *Nucleic Acids Res.*, vol. 27, 1555-1557.

Muyrers, et al., (2001); "Techniques: Recobminogenic engineering—new options for cloning and manipulting DNA"; *Trends in Biochemical Sciences*, vol. 26, No. 5, 325-331.

Resnick, et al., (1989); "The Pathophysiology of Urinary Incontinence Among Institutinalized Elderly Persons"; *The New England Journal of Medicine*; vol. 320, No. 1, 1-7.

Salier, et al., (1996); "The inter-60 -inhibitor family: from structure to regulation"; *Biochem Journal*; vol. 315, 1-9.

Stow, N.D., (1992); "Herpes simplex virus type 1 origin-dependent DNA replication in insect cells using recombinant baculoviruses"; *J. Gen. Virol.*; vol. 73; 313-321.

Szybalska, et al., (1962); "Genetics of Human Cell Lines, IV. DNA-Mediated Heritable Transformation of a Biochemical Trait"; *Proc. Natl. Sci. USA*; vol. 48, 2026-2034.

Thompson, et al., (1989); "Germ Line Transmission and Expression of a Corrected HPRT Gene Produced by Gene Targeting in Embryonic Stem Cells"; *Cell*; vol. 56; 313-321.

Yu, et al., (2000); "An efficient recombination system for chromosome engeineering in *Escherichia coli*"; *Proc. Natl Acad. Sci USA*; vol. 97; 5978-5983.

Van Der Putten, et al., (1985); "efficient insertion of genes into the mouse germ line via retroviral vectors"; *Proc. Natl. Acad. Sci. USA*; vol. 82; 6148-6152.

Wu et al., (1991); "Receptor-mediated Gene Delivery *in Vivo*"; *J. Biol. Chem.*; vol. 266, 14338-14342.

Wu et al., (1988); "Receptor-mediated Gene Delivery and Expression *in Vivo*"; *J. Biol. Chem*; vol. 263, No. 29, 14621-14624.

Wu, et al., (1994); "Incorporation of Adenovirus into a Ligand-based DNA Carrier System Results in Retention of Original Receptor Specificity and Enhances Targeted Gene Expression"; *J. Biol. Chem.*; vol. 269, No. 15, 11542-11546.

Zenke, et al., (1990); "Receptor-mediated endocytosis of transferrin-polycation conjugates: An efficient way to introduce DNA into hematopoietic cells"; *Proc. Natl. Acad. Sci. USA*; vol. 87, 3655-3659.

Zhang, et al., (2000); DNA cloning by homologous recombination in *Escherichia coli*; *Nt. Biotechnol.*; vol. 18, 1314-1317.

NCBI Sequence, Accession M20165; www.ncbi.nlm.nih.gov; printed Aug. 15, 2002.

NCBI Sequence, Accession NP_044613; www.ncbi.nlm.nih.gov; printed Aug. 15, 2002.

Wigler, Michael, et al.: "Transfer of Purified Herpes Virus Thymidine Kinase Gene to Cultured Mouse Cells"; Cell; vol. 11; pp. 223-232; May 1977.

* cited by examiner

SEQUENCE LISTING

<160> NUMBER OF SEQ ID NOS: 6

<210> SEQ ID NO 1
<211> LENGTH: 1881
<212> TYPE: DNA
<213> ORGANISM: Herpes simpex virus 1
<300> PUBLICATION INFORMATION:
<308> DATABASE ACCESSION NUMBER: NC 001806
<309> DATABASE ENTRY DATE: 2003-08-18
<313> RELEVANT RESIDUES: (1)..(1881)

<400> SEQUENCE: 1

```
atggagtcca cggtaggccc agcatgtccg ccgggacgca ccgtgactaa gcgtccctgg      60
gccctggccg aggacacccc tcgtggcccc gacagccccc ccaagcgccc ccgccctaac     120
agtcttccgc tgacaaccac cttccgtccc ctgccccccc cacccccagac gacatcagct     180 gtggacccga gctcccattc gcccgttaac ccccacgtg atcagcacgc caccgacacc      240
gcagacgaaa agccccgggc cgcgtcgccg gcactttctg acgcctcagg gcctccgacc      300
ccagacattc cgctatctcc tgggggcacc cacgcccgcg acccggacgc cgatcccgac      360
tccccggacc ttgactctat gtggtcggcg tcggtgatcc ccaacgcgct gccctcccat     420
atactagccg agacgttcga gcgccacctg cgcgggttgc tgcgcggcgt ccgcgcccct     480
ctggccatcg gtccctctg ggcccgcctg gattatctgt gttccctggc cgtggtcctc      540
gaggaggcgg gtatggtgga ccgcggactc ggtcggcacc tatggcgcct gacgcgccgc      600
gggcccccgg ccgccgcgga cgccgtggcg ccccggcccc tcatggggtt ttacgaggcg      660
```

-continued

```
gccacgcaaa accaggccga ctgccagcta tgggccctgc tccggcgggg cctcacgacc      720
gcatccaccc tccgctgggg cccccagggt ccgtgtttct cgcccagtg gctgaagcac       780
aacgccagcc tgcggccgga tgtacagtct tcggcggtga tgttcggcg ggtgaacgag       840
ccgacggccc gaagcctgct gtttcgctac tgcgtgggcc gcgcggacga cggcggcgag      900
gccggcgccg acacgcggcg ctttatcttc cacgaaccca gcgacctcgc cgaagagaac      960
gtgcatacgt gtgggtcct catggacggt cacacgggga tggtcgggc gtccctggat      1020
attctcgtct gtcctcggga cattcacggc tacctggccc cagtccccaa gaccccctg     1080
gccttttacg aggtcaaatg ccgggccaag tacgctttcg accccatgga ccccagcgac    1140
cccacggcct ccgcgtacga ggacttgatg gcacaccggt ccccggaggc gttccgggca    1200
tttatccggt cgatcccgaa gcccagcgt cgatacttcg cgcccgggcg cgtccccggc    1260
ccggaggagg ctctcgtcac gcaagaccag gcctggtcag aggcccacgc tcgggcgaa    1320
aaaaggcggt gctccgccgc ggatcgggcc ttggtggagt taaatagcgg cgttgtctcg    1380
gaggtgcttc tgtttggcgc cccgacctc ggacgccaca ccatctcccc cgtgtcctgg    1440
agctccgggg atctggtccg ccgcgagccc gtcttcgcga accccgtca cccgaacttt    1500
aagcagatct tggtgcaggg ctacgtgctc gacagccact tccccgactg cccccccac    1560
ccgcatctgg tgacgtttat cggcaggcac cgcaccagcg cggaggaggg cgtaacgttc    1620
cgcctggagg acggcgccgg ggctctcggg gccgcaggac ccagcaaggc gtccattctc    1680
ccgaaccagg ccgttccgat cgccctgatc attacccccg tccgcatcga tccggagatc    1740
tataaggcca tccagcgaag cagccgcctg gcattcgacg acacgctcgc cgagctatgg    1800
gcctctcgtt ctccggggcc cggccctgct gctgccgaaa caacgtcctc atcaccgacg    1860
acggggaggt cgtctcgctg a                                              1881
```

<210> SEQ ID NO 2
<211> LENGTH: 626
<212> TYPE: PRT
<213> ORGANISM: Herpes simpex virus 1
<300> PUBLICATION INFORMATION:
<308> DATABASE ACCESSION NUMBER: GI 119693
<309> DATABASE ENTRY DATE: 1992-05-01
<313> RELEVANT RESIDUES: (1)..(626)

<400> SEQUENCE: 2

```
Met Glu Ser Thr Val Gly Pro Ala Cys Pro Pro Gly Arg Thr Val Thr
1               5                   10                  15

Lys Arg Pro Trp Ala Leu Ala Glu Asp Thr Pro Arg Gly Pro Asp Ser
            20                  25                  30

Pro Pro Lys Arg Pro Arg Pro Asn Ser Leu Pro Leu Thr Thr Thr Phe
        35                  40                  45

Arg Pro Leu Pro Pro Pro Gln Thr Thr Ser Ala Val Asp Pro Ser
    50                  55                  60

Ser His Ser Pro Val Asn Pro Pro Arg Asp Gln His Ala Thr Asp Thr
65                  70                  75                  80

Ala Asp Glu Lys Pro Arg Ala Ala Ser Pro Ala Leu Ser Asp Ala Ser
                85                  90                  95

Gly Pro Pro Thr Pro Asp Ile Pro Leu Ser Pro Gly Thr His Ala
            100                 105                 110

Arg Asp Pro Asp Ala Asp Pro Asp Ser Pro Asp Leu Asp Ser Met Trp
        115                 120                 125

Ser Ala Ser Val Ile Pro Asn Ala Leu Pro Ser His Ile Leu Ala Glu
```

```
            130                 135                 140
Thr Phe Glu Arg His Leu Arg Gly Leu Leu Arg Gly Val Arg Ala Pro
145                 150                 155                 160

Leu Ala Ile Gly Pro Leu Trp Ala Arg Leu Asp Tyr Leu Cys Ser Leu
                165                 170                 175

Ala Val Val Leu Glu Glu Ala Gly Met Val Asp Arg Gly Leu Gly Arg
                180                 185                 190

His Leu Trp Arg Leu Thr Arg Gly Pro Pro Ala Ala Ala Asp Ala
                195                 200                 205

Val Ala Pro Arg Pro Leu Met Gly Phe Tyr Glu Ala Ala Thr Gln Asn
210                 215                 220

Gln Ala Asp Cys Gln Leu Trp Ala Leu Leu Arg Arg Gly Leu Thr Thr
225                 230                 235                 240

Ala Ser Thr Leu Arg Trp Gly Pro Gln Gly Pro Cys Phe Ser Pro Gln
                245                 250                 255

Trp Leu Lys His Asn Ala Ser Leu Arg Pro Asp Val Gln Ser Ser Ala
                260                 265                 270

Val Met Phe Gly Arg Val Asn Glu Pro Thr Ala Arg Ser Leu Leu Phe
                275                 280                 285

Arg Tyr Cys Val Gly Arg Ala Asp Asp Gly Gly Glu Ala Gly Ala Asp
                290                 295                 300

Thr Arg Arg Phe Ile Phe His Glu Pro Ser Asp Leu Ala Glu Glu Asn
305                 310                 315                 320

Val His Thr Cys Gly Val Leu Met Asp Gly His Thr Gly Met Val Gly
                325                 330                 335

Ala Ser Leu Asp Ile Leu Val Cys Pro Arg Asp Ile His Gly Tyr Leu
                340                 345                 350

Ala Pro Val Pro Lys Thr Pro Leu Ala Phe Tyr Glu Val Lys Cys Arg
                355                 360                 365

Ala Lys Tyr Ala Phe Asp Pro Met Asp Pro Ser Asp Pro Thr Ala Ser
                370                 375                 380

Ala Tyr Glu Asp Leu Met Ala His Arg Ser Pro Glu Ala Phe Arg Ala
385                 390                 395                 400

Phe Ile Arg Ser Ile Pro Lys Pro Ser Val Arg Tyr Phe Ala Pro Gly
                405                 410                 415

Arg Val Pro Gly Pro Glu Glu Ala Leu Val Thr Gln Asp Gln Ala Trp
                420                 425                 430

Ser Glu Ala His Ala Ser Gly Glu Lys Arg Arg Cys Ser Ala Ala Asp
                435                 440                 445

Arg Ala Leu Val Glu Leu Asn Ser Gly Val Val Ser Glu Val Leu Leu
450                 455                 460

Phe Gly Ala Pro Asp Leu Gly Arg His Thr Ile Ser Pro Val Ser Trp
465                 470                 475                 480

Ser Ser Gly Asp Leu Val Arg Arg Glu Pro Val Phe Ala Asn Pro Arg
                485                 490                 495

His Pro Asn Phe Lys Gln Ile Leu Val Gln Gly Tyr Val Leu Asp Ser
                500                 505                 510

His Phe Pro Asp Cys Pro Pro His Pro His Leu Val Thr Phe Ile Gly
                515                 520                 525

Arg His Arg Thr Ser Ala Glu Glu Gly Val Thr Phe Arg Leu Glu Asp
                530                 535                 540

Gly Ala Gly Ala Leu Gly Ala Gly Pro Ser Lys Ala Ser Ile Leu
545                 550                 555                 560
```

```
Pro Asn Gln Ala Val Pro Ile Ala Leu Ile Ile Thr Pro Val Arg Ile
                565                 570                 575

Asp Pro Glu Ile Tyr Lys Ala Ile Gln Arg Ser Ser Arg Leu Ala Phe
            580                 585                 590

Asp Asp Thr Leu Ala Glu Leu Trp Ala Ser Arg Ser Pro Gly Pro Gly
        595                 600                 605

Pro Ala Ala Ala Glu Thr Thr Ser Ser Ser Pro Thr Thr Gly Arg Ser
    610                 615                 620

Ser Arg
625

<210> SEQ ID NO 3
<211> LENGTH: 4420
<212> TYPE: DNA
<213> ORGANISM: Herpes simpex virus 1
<300> PUBLICATION INFORMATION:
<308> DATABASE ACCESSION NUMBER: M20165
<309> DATABASE ENTRY DATE: 1994-04-19
<313> RELEVANT RESIDUES: (1)..(4420)

<400> SEQUENCE: 3
```

| | | | | | |
|---|---|---|---|---|---|
| cggatccggg | cggcgagctg | ctgcgcggcg | ccccggccgg | cggcccggtt | tattcgcgtc | 60 |
| ggcccggccg | gccgggctta | tggaccgccg | gcggccgaca | ggagcgtgac | gtagccggtg | 120 |
| ggcgtggccg | ctattataaa | aaaagtgaga | acgcgaagcg | ttcgcacttt | gtcctaataa | 180 |
| tatatatatt | attaggacaa | agtgcgaacg | cttcgcgttc | tcactttttt | tataatagcg | 240 |
| gccacgccca | ccggctgatg | acgcgcgggg | tgtgggaggg | gctggggcgg | tccggcacgc | 300 |
| ccccaggtaa | agtgtacata | taccaaccgc | atatcagacg | cacccggccc | ggagcacctg | 360 |
| accgtaagca | tctgtgcctc | tcgcagggac | cccgcgttgc | cagccgccgg | ggttcatcgg | 420 |
| cacccccgtgg | ttacccgggg | gttgtcggtg | aagggtaggg | attcattccc | caaccccggt | 480 |
| ctcccaccct | ccccttgacc | gtcgccgccc | cccccccgg | attttgacgc | tcgggagaca | 540 |
| tacctcgtcg | ggcgtccgtc | gtcgtgccgg | gattacctcc | gtttgcggac | cgattgccag | 600 |
| gaggacatgg | agacaaagcc | caagacggca | accaccatca | aggtcccccc | cgggcccctg | 660 |
| ggatacgtgt | acgctcgcgc | gtgtccgtcc | gaaggcatcg | agcttctggc | gttactgtcg | 720 |
| gcgcgcagcg | gcgatgccga | cgtcgccgtg | gcgcccctgg | tcgtgggcct | gaccgtggag | 780 |
| agcggctttg | aggccaacgt | agccgtggtc | gtgggttctc | gcacgacggg | gctcggggt | 840 |
| accgcggtgt | ccctgaaact | gacgccatcg | cactacagct | cgtccgtgta | cgtctttcac | 900 |
| ggcggccggc | acctggaccc | cagcacccag | gccccaaacc | tgacgcgact | ctgcgagcgg | 960 |
| gcacgccgcc | attttggctt | tcggactac | acccccggc | ccggcgacct | caaacacgag | 1020 |
| acgacggggg | aggcgctgtg | tgagcgcctc | ggcctggacc | cggaccgcgc | cctcctgtat | 1080 |
| ctggtcgtta | ccgagggctt | caaggaggcc | gtgtgcatca | acaacacctt | tctgcacctg | 1140 |
| ggaggctcgg | acaaggtaac | cataggcggg | gcggaggtgc | accgcatacc | cgtgtatccg | 1200 |
| ttgcagctgt | tcatgccgga | ttttagccgg | gtcatcgccg | agccgttcaa | cgccaaccac | 1260 |
| cgatcgatcg | gggagaattt | tacctacccg | cttccgtttt | ttaaccgccc | cctcaaccgc | 1320 |
| ctcctgttcg | aggcggtcgt | gggacccgcc | gccgtgcac | tgcgatgccg | aaacgtggac | 1380 |
| gccgtggccc | gcgcggccgc | ccacctggcg | tttgacgaaa | accacgaggg | cgccgccctc | 1440 |
| cccgccgaca | ttcgcgttcac | ggccttcgaa | gccagccagg | gtaagacccc | gcggggtggg | 1500 |
| cgcgacggcg | gcggcaaggg | cccggcgggc | gggttcgaac | agcgcctggc | ctccgtcatg | 1560 |

```
gccggagacg ccgccctggc cctcgagtct atcgtgtcga tggccgtctt cgacgagccg    1620
cccaccgaca tctccgcgtg gccgctgtgc gagggccagg acacggccgc ggcccgcgcc    1680
aacgccgtcg gggcgtacct ggcgcgcgcc gcgggactcg tgggggccat ggtatttagc    1740
accaactcgg ccctccatct caccgaggtg gacgacgccg gtccggcgga cccaaaggac    1800
cacagcaaac cctccttttta ccgcttcttc ctcgtgcccg ggacccacgt ggcggccaac    1860
ccacaggtgg accgcgaggg acacgtggtg cccgggttcg agggtcggcc caccgcgccc    1920
ctcgtcggcg gaacccagga atttgccggc gagcacctgg ccatgctgtg tgggttttcc    1980
ccggcgctgc tggccaagat gctgttttac ctggagcgct gcgacggcgg cgtgatcgtc    2040
gggcgccagg agatggacgt gtttcgatac gtcgcggact ccaaccagac cgacgtgccc    2100
tgcaacctgt gcaccttcga cacgcgccac gcctgcgtac acacgacgct catgcgcctc    2160
cgggcgcgcc atcccaagtt cgccagcgcc gcccgcggag ccatcggcgt cttcgggacc    2220
atgaacagca tgtacagcga ctgcgacgtg ctgggaaact acgccgcctt ctcggccctg    2280
aagcgcgcgg acggatccga gaccgcccgg accatcatgc aggagacgta ccgcgcggcg    2340
accgagcgcg tcatggccga actcgagacc ctgcagtacg tggaccaggc ggtccccacg    2400
gccatggggc ggctggagac catcatcacc aaccgcgagg ccctgcatac ggtggtgaac    2460
aacgtcaggc aggtcgtgga ccgcgaggtg gagcagctga tgcgcaacct ggtggagggg    2520
aggaacttca gtttcgcga cggtctgggc gaggccaacc acgccatgtc cctgacgctg    2580
gacccgtacg cgtgcgggcc atgccccctg cttcagcttc tcgggcggcg atccaacctc    2640
gccgtgtatc aggacctggc cctgagccag tgccacgggg tgttcgccgg gcagtcggtc    2700 gagggggcgca actttcgcaa tcaattccaa ccggtgctgc ggcggcgcgt gatggacatg    2760
tttaacaacg ggtttctgtc ggccaaaacg ctgacggtcg cgctctcgga ggggggcggct    2820 atctgcgccc ccagcctaac ggccggccag acggcccccg ccgagagcag cttcgagggc    2880
gacgttgccc gcgtgaccct gggggtttccc aaggagctgc gcgtcaagag ccgcgtgttg    2940
ttcgcgggcg cgagcgccaa cgcgtccgag gccgccaagg cgcgggtcgc cagcctccag    3000
agcgcctacc agaagcccga caagcgcgtg gacatcctcc tcggaccgct gggctttctg    3060
ctgaagcagt tccacgcggc catcttcccc aacggcaagc cccgggggtc caaccagccg    3120
aacccgcagt ggttctggac ggccctccaa cgcaaccagc ttcccgcccg gctcctgtcg    3180
cgcgaggaca tcgagaccat cgcgttcatt aaaaagtttt ccctggacta cggcgcgata    3240
aactttatta acctggcccc caacaacgtg agcgagctgg cgatgtacta catggcaaac    3300
cagattctgc ggtactgcga tcactcgaca tacttcatca acaccctcac ggccatcatc    3360
gcggggtccc gccgtccccc cagcgtgcag gcggcggccg cgtggtccgc gcagggcggg    3420
gcgggcctgg aggccgggc ccgcgcgctg atggacgccg tggacgcgca tccgggcgcg    3480
tggacgtcca tgttcgccag ctgcaacctg ctgcggcccg tcatggcggc gcgccccatg    3540 gtcgtgtttgg ggttgagcat cagcaaatac tacggcatgg ccggcaacga ccgtgtgttt    3600
caggccggga actgggccag cctgatgggc ggcaaaaacg cgtgcccgct ccttattttt    3660
gaccgcaccc gcaagttcgt cctggcctgt cccccgggccg ggtttgtgtg cgcggcctcg    3720
aacctcggcg gcggagcgca cgaaagctcg ctgtgcgagc agctccgggg cattatctcc    3780
gagggcgggg cggccgtcgc cagtagcgtt ttcgtggcga ccgtgaaaag cctgggggccc    3840 cgcacccagc agctgcagat cgaggactgg ctggcgctcc tggaggacga gtacctaagc    3900
```

-continued

```
gaggagatga tggagctgac cgcgcgtgcc ctggagcgcg gcaacggcga gtggtcgacg    3960
gacgcggccc tggaggtggc gcacgaggcc gaggccctag tcagccaact cggcaacgcc    4020
ggggaggtgt ttaactttgg ggattttggc tgcgaggacg acaacgcgac gccgttcggc    4080
ggcccggggg ccccgggacc ggcatttgcc ggccgcaaac gggcgttcca cggggatgac    4140
ccgtttgggg aggggccccc cgacaaaaag ggagacctga cgttggatat gctgtgaggg    4200 gttgggggt gggggaacct agggcggggc ggggaatgtg tgtaaaataa attattgcta    4260
cgacatccgt gcttgtttgt gttccgtgtc tatatctctg ggcgggccgt gattcctctc    4320
cgcggtgtct gggaatagaa cagaaacgca cgcgccgccg actcccggct tgccggtcgg    4380
cgggcccgcg ggaggccgcc ccgaagaggg ggaccccggg                         4420
```

<210> SEQ ID NO 4
<211> LENGTH: 1196
<212> TYPE: PRT
<213> ORGANISM: Herpes simpex virus 1
<300> PUBLICATION INFORMATION:
<308> DATABASE ACCESSION NUMBER: M20165
<309> DATABASE ENTRY DATE: 1994-04-19
<313> RELEVANT RESIDUES: (1)..(1196)

<400> SEQUENCE: 4

```
Met Glu Thr Lys Pro Lys Thr Ala Thr Thr Ile Lys Val Pro Pro Gly
1               5                   10                  15

Pro Leu Gly Tyr Val Tyr Ala Arg Ala Cys Pro Ser Glu Gly Ile Glu
            20                  25                  30

Leu Leu Ala Leu Leu Ser Ala Arg Ser Gly Asp Ala Asp Val Ala Val
        35                  40                  45

Ala Pro Leu Val Val Gly Leu Thr Val Glu Ser Gly Phe Glu Ala Asn
    50                  55                  60

Val Ala Val Val Gly Ser Arg Thr Gly Leu Gly Gly Thr Ala
65                  70                  75                  80

Val Ser Leu Lys Leu Thr Pro Ser His Tyr Ser Ser Val Tyr Val
                85                  90                  95

Phe His Gly Gly Arg His Leu Asp Pro Ser Thr Gln Ala Pro Asn Leu
            100                 105                 110

Thr Arg Leu Cys Glu Arg Ala Arg Arg His Phe Gly Phe Ser Asp Tyr
        115                 120                 125

Thr Pro Arg Pro Gly Asp Leu Lys His Glu Thr Thr Gly Glu Ala Leu
    130                 135                 140

Cys Glu Arg Leu Gly Leu Asp Pro Asp Arg Ala Leu Leu Tyr Leu Val
145                 150                 155                 160

Val Thr Glu Gly Phe Lys Glu Ala Val Cys Ile Asn Asn Thr Phe Leu
                165                 170                 175

His Leu Gly Gly Ser Asp Lys Val Thr Ile Gly Gly Ala Glu Val His
            180                 185                 190

Arg Ile Pro Val Tyr Pro Leu Gln Leu Phe Met Pro Asp Phe Ser Arg
        195                 200                 205

Val Ile Ala Glu Pro Phe Asn Ala Asn His Arg Ser Ile Gly Glu Asn
    210                 215                 220

Phe Thr Tyr Pro Leu Pro Phe Asn Arg Pro Leu Asn Arg Leu Leu
225                 230                 235                 240

Phe Glu Ala Val Val Gly Pro Ala Ala Val Ala Leu Arg Cys Arg Asn
                245                 250                 255

Val Asp Ala Val Ala Arg Ala Ala Ala His Leu Ala Phe Asp Glu Asn
```

-continued

```
                260                 265                 270
His Glu Gly Ala Ala Leu Pro Ala Asp Ile Thr Phe Thr Ala Phe Glu
            275                 280                 285
Ala Ser Gln Gly Lys Thr Pro Arg Gly Arg Asp Gly Gly Gly Lys
        290                 295                 300
Gly Pro Ala Gly Gly Phe Glu Gln Arg Leu Ala Ser Val Met Ala Gly
305                 310                 315                 320
Asp Ala Ala Leu Ala Leu Glu Ser Ile Val Ser Met Ala Val Phe Asp
                325                 330                 335
Glu Pro Pro Thr Asp Ile Ser Ala Trp Pro Leu Cys Glu Gly Gln Asp
            340                 345                 350
Thr Ala Ala Ala Arg Ala Asn Ala Val Gly Ala Tyr Leu Ala Arg Ala
                355                 360                 365
Ala Gly Leu Val Gly Ala Met Val Phe Ser Thr Asn Ser Ala Leu His
            370                 375                 380
Leu Thr Glu Val Asp Asp Ala Gly Pro Ala Asp Pro Lys Asp His Ser
385                 390                 395                 400
Lys Pro Ser Phe Tyr Arg Phe Phe Leu Val Pro Gly Thr His Val Ala
                405                 410                 415
Ala Asn Pro Gln Val Asp Arg Glu Gly His Val Val Pro Gly Phe Glu
            420                 425                 430
Gly Arg Pro Thr Ala Pro Leu Val Gly Thr Gln Glu Phe Ala Gly
            435                 440                 445
Glu His Leu Ala Met Leu Cys Gly Phe Ser Pro Ala Leu Leu Ala Lys
            450                 455                 460
Met Leu Phe Tyr Leu Glu Arg Cys Asp Gly Gly Val Ile Val Gly Arg
465                 470                 475                 480
Gln Glu Met Asp Val Phe Arg Tyr Val Ala Asp Ser Asn Gln Thr Asp
                485                 490                 495
Val Pro Cys Asn Leu Cys Thr Phe Asp Thr Arg His Ala Cys Val His
            500                 505                 510
Thr Thr Leu Met Arg Leu Arg Ala Arg His Pro Lys Phe Ala Ser Ala
            515                 520                 525
Ala Arg Gly Ala Ile Gly Val Phe Gly Thr Met Asn Ser Met Tyr Ser
530                 535                 540
Asp Cys Asp Val Leu Gly Asn Tyr Ala Ala Phe Ser Ala Leu Lys Arg
545                 550                 555                 560
Ala Asp Gly Ser Glu Thr Ala Arg Thr Ile Met Gln Glu Thr Tyr Arg
                565                 570                 575
Ala Ala Thr Glu Arg Val Met Ala Glu Leu Glu Thr Leu Gln Tyr Val
                580                 585                 590
Asp Gln Ala Val Pro Thr Ala Met Gly Arg Leu Glu Thr Ile Ile Thr
            595                 600                 605
Asn Arg Glu Ala Leu His Thr Val Val Asn Val Arg Gln Val Val
            610                 615                 620
Asp Arg Glu Val Glu Gln Leu Met Arg Asn Leu Val Glu Gly Arg Asn
625                 630                 635                 640
Phe Lys Phe Arg Asp Gly Leu Gly Glu Ala Asn His Ala Met Ser Leu
                645                 650                 655
Thr Leu Asp Pro Tyr Ala Cys Gly Pro Cys Pro Leu Leu Gln Leu Leu
            660                 665                 670
Gly Arg Arg Ser Asn Leu Ala Val Tyr Gln Asp Leu Ala Leu Ser Gln
            675                 680                 685
```

-continued

```
Cys His Gly Val Phe Ala Gly Gln Ser Val Glu Gly Arg Asn Phe Arg
    690                 695                 700

Asn Gln Phe Gln Pro Val Leu Arg Arg Arg Val Met Asp Met Phe Asn
705                 710                 715                 720

Asn Gly Phe Leu Ser Ala Lys Thr Leu Thr Val Ala Leu Ser Glu Gly
                725                 730                 735

Ala Ala Ile Cys Ala Pro Ser Leu Thr Ala Gly Gln Thr Ala Pro Ala
            740                 745                 750

Glu Ser Ser Phe Glu Gly Asp Val Ala Arg Val Thr Leu Gly Phe Pro
        755                 760                 765

Lys Glu Leu Arg Val Lys Ser Arg Val Leu Phe Ala Gly Ala Ser Ala
    770                 775                 780

Asn Ala Ser Glu Ala Ala Lys Ala Arg Val Ala Ser Leu Gln Ser Ala
785                 790                 795                 800

Tyr Gln Lys Pro Asp Lys Arg Val Asp Ile Leu Leu Gly Pro Leu Gly
                805                 810                 815

Phe Leu Leu Lys Gln Phe His Ala Ala Ile Phe Pro Asn Gly Lys Pro
            820                 825                 830

Pro Gly Ser Asn Gln Pro Asn Pro Gln Trp Phe Trp Thr Ala Leu Gln
        835                 840                 845

Arg Asn Gln Leu Pro Ala Arg Leu Leu Ser Arg Glu Asp Ile Glu Thr
    850                 855                 860

Ile Ala Phe Ile Lys Lys Phe Ser Leu Asp Tyr Gly Ala Ile Asn Phe
865                 870                 875                 880

Ile Asn Leu Ala Pro Asn Asn Val Ser Glu Leu Ala Met Tyr Tyr Met
                885                 890                 895

Ala Asn Gln Ile Leu Arg Tyr Cys Asp His Ser Thr Tyr Phe Ile Asn
            900                 905                 910

Thr Leu Thr Ala Ile Ile Ala Gly Ser Arg Arg Pro Pro Ser Val Gln
        915                 920                 925

Ala Ala Ala Ala Trp Ser Ala Gln Gly Gly Ala Gly Leu Glu Ala Gly
    930                 935                 940

Ala Arg Ala Leu Met Asp Ala Val Asp Ala His Pro Gly Ala Trp Thr
945                 950                 955                 960

Ser Met Phe Ala Ser Cys Asn Leu Leu Arg Pro Val Met Ala Ala Arg
                965                 970                 975

Pro Met Val Val Leu Gly Leu Ser Ile Ser Lys Tyr Tyr Gly Met Ala
            980                 985                 990

Gly Asn Asp Arg Val Phe Gln Ala Gly Asn Trp Ala Ser Leu Met Gly
        995                 1000                1005

Gly Lys Asn Ala Cys Pro Leu Leu Ile Phe Asp Arg Thr Arg Lys
    1010                1015                1020

Phe Val Leu Ala Cys Pro Arg Ala Gly Phe Val Cys Ala Ala Ser
    1025                1030                1035

Asn Leu Gly Gly Gly Ala His Glu Ser Ser Leu Cys Glu Gln Leu
    1040                1045                1050

Arg Gly Ile Ile Ser Glu Gly Gly Ala Ala Val Ala Ser Ser Val
    1055                1060                1065

Phe Val Ala Thr Val Lys Ser Leu Gly Pro Arg Thr Gln Gln Leu
    1070                1075                1080

Gln Ile Glu Asp Trp Leu Ala Leu Leu Glu Asp Glu Tyr Leu Ser
    1085                1090                1095
```

```
-continued

Glu  Glu  Met  Met  Glu  Leu  Thr  Ala  Arg  Ala  Leu  Glu  Arg  Gly  Asn
     1100                     1105                    1110

Gly  Glu  Trp  Ser  Thr  Asp  Ala  Ala  Leu  Glu  Val  Ala  His  Glu  Ala
     1115                     1120                    1125

Glu  Ala  Leu  Val  Ser  Gln  Leu  Gly  Asn  Ala  Gly  Glu  Val  Phe  Asn
     1130                     1135                    1140

Phe  Gly  Asp  Phe  Gly  Cys  Glu  Asp  Asp  Asn  Ala  Thr  Pro  Phe  Gly
     1145                     1150                    1155

Gly  Pro  Gly  Ala  Pro  Gly  Pro  Ala  Phe  Ala  Gly  Arg  Lys  Arg  Ala
     1160                     1165                    1170

Phe  His  Gly  Asp  Asp  Pro  Phe  Gly  Glu  Gly  Pro  Pro  Asp  Lys  Lys
     1175                     1180                    1185

Gly  Asp  Leu  Thr  Leu  Asp  Met  Leu
     1190                     1195

<210> SEQ ID NO 5
<211> LENGTH: 30
<212> TYPE: DNA
<213> ORGANISM: Artificial
<220> FEATURE:
<223> OTHER INFORMATION: M13 DNA primer

<400> SEQUENCE: 5
gtcggtgacg gtgataattc acctttaatg                                        30

<210> SEQ ID NO 6
<211> LENGTH: 30
<212> TYPE: DNA
<213> ORGANISM: Artificial
<220> FEATURE:
<223> OTHER INFORMATION: M13 DNA primer

<400> SEQUENCE: 6
cattaaaggt gaattatcac cgtcaccgac                                        30
```

VIRAL RECOMBINASES, RELATED ARTICLES, AND METHODS OF USE THEREOF

CROSS REFERENCE TO RELATED APPLICATIONS

This application claims priority from Provisional Application Ser. No. 60/408,092, filed Sep. 4, 2002, which is incorporated herein by reference in its entirety.

STATEMENT REGARDING FEDERALLY SPONSORED RESEARCH & DEVELOPMENT

The U.S. Government has certain rights in this invention pursuant to Public Health Service Grant Nos. AI21747 and AI37549 awarded by the National Institute of Health.

BACKGROUND

The present disclosure relates to recombinases and methods of using homologous recombination.

In the past several years, the genome project has provided knowledge that was once thought to be nearly impossible to obtain. Thanks to this endeavor, we now have a window into the very code of life. One of the original promises of this work was that having the actual sequences of the human genome would enable the detection of differences in those sequences that lead to disease or malfunction, and may eventually lead to correction of such defects. However, because the genomes of higher organisms are both complex and large, their manipulation is not a simple matter.

While techniques such as cloning site-specific mutations using DNA restriction enzymes have been successful for manipulating DNA fragments, such techniques are not well-suited for manipulation of large DNA fragments, i.e., fragments the size of mammalian genes. One method that has been used to manipulate large DNA fragments is recombination, particularly site-specific recombination. Recombination is the exchange of DNA segments along two different strands of DNA. In site-specific recombination, DNA strand exchange occurs at a specific site, for example, as in the integration of phage lambda into the E. coli chromosome and the excision of lambda DNA from it. Site-specific recombination involves specific sequences of both the donor and target DNA segments. In the Cre-loxP and FLP-FRT systems, for example, recombination involves short (i.e., less than about 50 base pairs), inverted repeat sequences. Within these sequences, the homology between the DNA sequences is necessary for the recombination event, but not sufficient for it. Site-specific recombination requires enzymes or multi-enzyme complexes, often called recombinases. In site-specific recombination, recombinases generally cannot recombine other pairs of homologous (or nonhomologous) sequences, but act specifically on particular DNA sequences. Site-specific recombination has been proposed as one method to integrate transfected DNA at chromosomal locations having specific recognition sites. Because this approach requires the presence of specific target DNA sequence and recombinase combinations, its utility for targeting recombination events at a particular chromosomal location is limited.

Homologous recombination (or general recombination), in contrast, is defined as the exchange of homologous segments anywhere along a length of two DNA molecules. A feature of homologous recombination is that a recombinase active for homologous recombination can often use any pair of homologous sequences as substrates, although some types of sequence may be somewhat favored over others.

Several recombinases that catalyze homologous pairing and/or strand exchange in vitro have been purified and at least partially characterized, including: E. coli recA protein, the phage T4 uvsX protein, and the red protein from Ustilago maydis. Recombinases, such as the recA protein of E. coli, are proteins that promote strand pairing and exchange in such important cellular processes as the SOS repair response, DNA repair, and efficient genetic recombination in E. coli. RecA can catalyze homologous pairing of a linear duplex DNA and a homologous single strand DNA in vitro.

One drawback to the use of previously characterized recombinases such as recA is that these proteins are from prokaryotes and simple eukaryotes, and may not be applicable to recombination in higher eukaryotes such as mammals. There thus remains a need for compositions and methods for gene manipulation using homologous recombination that are suitable for use in mammalian hosts.

BRIEF SUMMARY

In one embodiment, a purified Herpes simplex virus recombinase comprises an alkaline nuclease and a single stranded DNA binding polypeptide, wherein the recombinase has polynucleotide strand exchange activity.

In another aspect, a host cell comprises a Herpes simplex virus recombinase, wherein the Herpes simplex virus recombinase is expressed from a first polynucleotide comprising a Herpes simplex virus-1 UL12 polynucleotide operatively linked to expression control sequences, and a second polynucleotide comprising a Herpes simplex virus-1 ICP8 polynucleotide operatively linked to expression control sequences.

A method of promoting homologous recombination, comprises contacting a purified Herpes simplex virus recombinase; a donor polynucleotide comprising a first donor homology region at a first end, a second donor homology region at a second end, and an exogenous sequence therebetween; and a target polynucleotide comprising a first donor homology region at a first end, a second donor homology region at a second end, and an endogenous sequence therebetween; wherein contacting is performed under conditions sufficient to promote homologous recombination. The herpes simplex virus recombinase comprises an alkaline nuclease and a single stranded DNA binding polypeptide and has polynucleotide strand exchange activity.

In another embodiment, a cloning kit, comprises a Herpes simplex virus recombinase, wherein the Herpes simplex virus recombinase comprises an alkaline nuclease and a single stranded DNA binding polypeptide, and wherein the recombinase has polynucleotide strand exchange activity; and a target polynucleotide comprising a first homology region at a first end, a second homology region at a second end, and an endogenous sequence therebetween.

A method of treating a eukaryotic host cell comprises delivering to the eukaryotic host cell a Herpes simplex virus recombinase, wherein the Herpes simplex virus recombinase comprises an alkaline nuclease and a single stranded DNA binding polypeptide, and wherein the recombinase has polynucleotide strand exchange activity; and a donor polynucleotide comprising a first donor homology region at a first end, a second donor homology region at a second end, and an exogenous sequence therebetween.

In another embodiment, a method of obtaining a transgenic non-human animal, comprises delivering to an embryonic stem cell or zygote a Herpes simplex virus recombinase, wherein the Herpes simplex virus recombinase comprises an alkaline nuclease and a single stranded DNA binding polypeptide; and a donor polynucleotide comprising a first homology region at a first end, a second homology region at a second end, and an exogenous sequence therebetween; wherein the exogenous sequence integrates into a genome of the embryonic stem cell or the zygote; and producing from the embryonic stem cell or the zygote a transgenic non-human animal.

A method of treating an organism comprises delivering to the organism a composition comprising a Herpes simplex virus recombinase; and a donor polynucleotide comprising a first homology region at a first end, a second homology region at a second end, and an exogenous sequence therebetween; wherein the Herpes simplex virus recombinase comprises an alkaline nuclease and a single stranded DNA binding polypeptide, and wherein the recombinase has polynucleotide strand exchange activity.

In another embodiment, a method of making a modified host cell comprises delivering to the host cell a composition comprising a Herpes simplex virus recombinase; and a donor polynucleotide comprising a first homology region at a first end, a second homology region at a second end, and an exogenous sequence therebetween; wherein the Herpes simplex virus recombinase comprises an alkaline nuclease and a single stranded DNA binding polypeptide, and wherein the recombinase has polynucleotide strand exchange activity.

BRIEF DESCRIPTION OF THE DRAWINGS

Referring now to the drawings wherein like elements are numbered alike in several FIGURES.

DETAILED DESCRIPTION OF THE PREFERRED EMBODIMENTS

Figure 1:
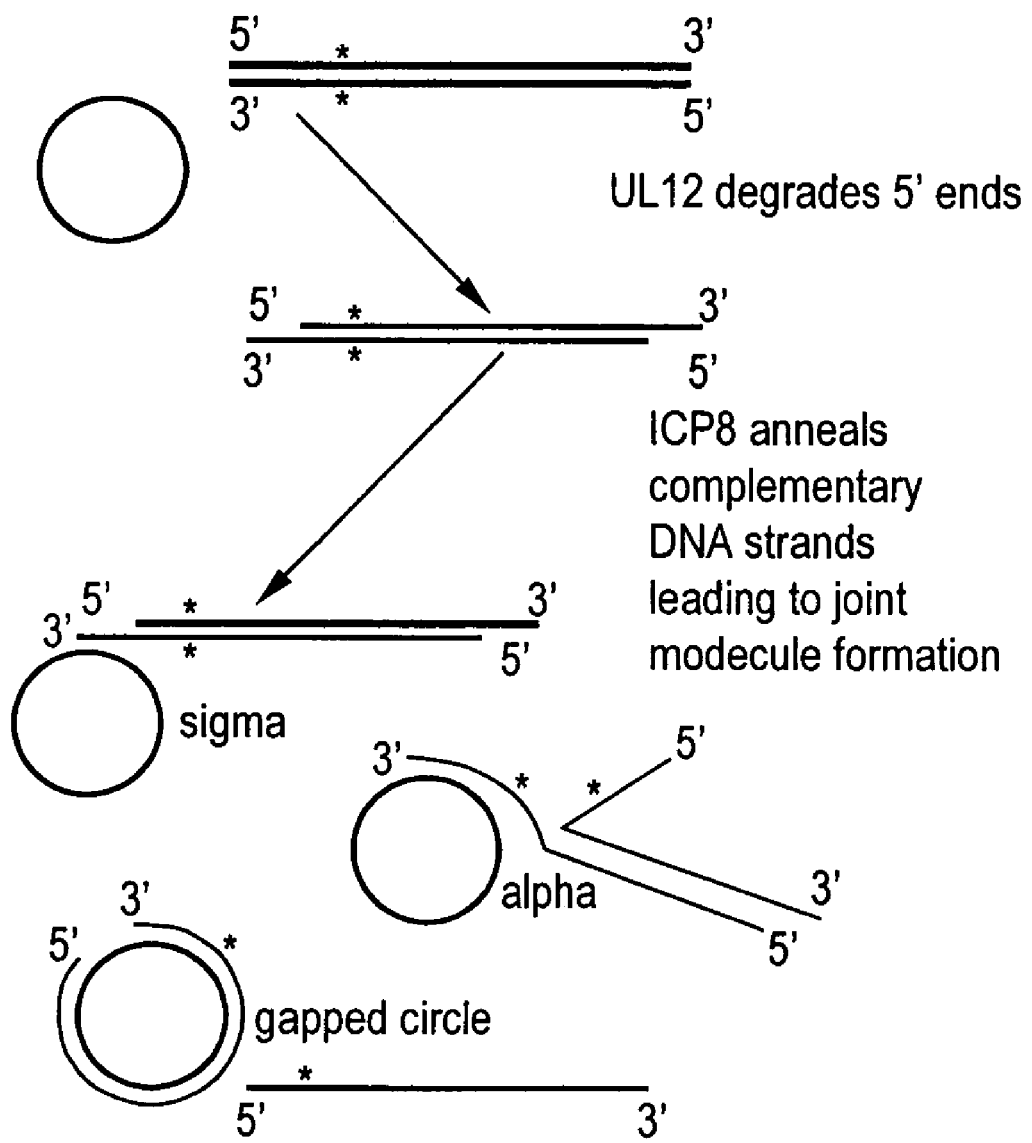
FIG. 1 shows a schematic representation of representative joint molecule products at different stages of strand exchange.

It has been unexpectedly discovered herein that the Herpes simplex virus type 1 (HSV-1) alkaline nuclease (encoded by the UL12 gene and hereinafter referred to as "UL12") and the HSV-1 single-strand DNA binding polypeptide (encoded by the ICP 8 gene and hereinafter referred to as "ICP8"; also known in the art as UL29) work together to effect DNA strand exchange. This synergistic activity of UL12 and ICP8 will hereinafter be referred to as the "HSV-1 recombinase". As used herein, HSV recombinase refers to a recombinase from a herpes virus, or related mammalian virus, comprising an alkaline nuclease and a single stranded DNA binding polypeptide.

HSV-1 is a double-stranded DNA virus with a 152 kilobase (kb) linear genome. Replication of HSV-1 DNA takes place in the host nucleus. The first step of viral replication involves the circularization of the genome. Shortly thereafter, replication intermediates appear as longer than unit length head-to-tail concatemers that have undergone genomic inversion. The genome concatemers are not linear, but rather consist of a mixture of complex structures such as Y- and X-shaped branches, replication bubbles, and tangled masses. The presence of these structures, and the inversion of the unique long (L) and unique short (S) genome segments, suggest that recombination plays a role in the replication of HSV-1 DNA. In fact, high levels of recombination are known to accompany HSV infection. While cellular recombinases may be involved in mediating some of these processes, the possibility has existed that HSV-1 encodes recombinases that can also participate.

Computer database searches revealed that the HSV-1 alkaline nuclease, encoded by the UL12 gene, shares homology with bacteriophage lambda Redα. The Redα protein is a 5' to 3' exonuclease required for recombination by bacteriophage lambda. This enzyme operates in conjunction with a single-strand DNA binding protein, lambda Redβ, which promotes single-strand DNA annealing. The lambda Red recombinase is functionally similar to *E. coli* RecE/RecT. These proteins are a paradigm for a class of recombinases that employ a strand-annealing protein and an exonuclease and do not require a high-energy cofactor. The model for recombination mediated by these proteins proposes that the exonuclease degrades DNA from a double-stranded (ds) end in the 5' to 3' direction, exposing a 3' single-stranded (ss) tail. This tail is bound by the single-strand DNA binding protein, which assembles a nucleoprotein filament that mediates annealing to a complementary single stranded DNA sequence.

Analogous to the interaction of lambda Redα and the single-strand DNA binding protein (SSB) lambda Redβ, UL12 interacts with the single-strand binding protein (SSB) of HSV-1, ICP8. Furthermore, ICP8 possesses strand-melting and strand annealing activities, and has been reported to mediate limited strand exchange. It has been demonstrated herein that, similar to Redα and Redβ, UL12 and ICP8 together mediate strand exchange.

In one embodiment, the invention includes a purified or isolated HSV recombinase, wherein the HSV recombinase comprises an alkaline nuclease and a single-stranded DNA binding polypeptide. The HSV recombinase is one that is active for polynucleotide strand exchange. The recombinase can be that from HSV-1 or can be comparable polypeptides from another Herpes virus or related virus such as, for example, Epstein-Barr virus, Cytomegalovirus, Varicella Voster virus, Human Herpes virus-6, Human Herpes virus-7, Human Herpes virus-8, Kaposi Sarcoma herpes virus and the like, and combinations comprising one or more of the foregoing viruses.

As used herein, a "purified" polypeptide, includes peptides substantially free of cellular material or other contaminating proteins from the cell or tissue source from which the protein is derived, or substantially free of chemical precursors or other chemicals when chemically synthesized. The language "substantially free of cellular material" includes preparations of polypeptide in which the polypeptide is separated from cellular components of the cells from which it is isolated or recombinantly produced. Thus, polypeptide that is substantially free of cellular material includes preparations of polypeptide having less than about 50%, 40%, 30%, 20%, 10%, or 5% (by dry weight) of heterologous protein (also referred to herein as a "contaminating protein"). When the polypeptide is recombinantly produced, it is also preferably substantially free of culture medium, i.e., culture medium represents less than about 80%, 60%, 50%, 40%, 30%, 20%, 10%, or 5% of the volume of the polypeptide preparation. A purified polypeptide can be a cell fraction which is substantially free of nucleic acids and/or cellular membrane fractions. When the polypeptide is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

An "isolated" protein is one that is not expressed from the viral genome in which the protein is found in nature. The term isolated encompasses protein preparations in which the protein is expressed from an expression vector. As such, an isolated HSV recombinase can be in a cell so long as the recombinase in the cell is expressed from an expression vector and not from the virus genome. For example, an HSV recombinase expressed from a baculovirus vector in an insect cell is considered to be an isolated HSV recombinase.

The recombinase can comprise the HSV-1 UL12 (nucleotide sequence SEQ ID NO:1; polypeptide sequence SEQ ID NO:2, Accession number NC 001806.1) and ICP8 polypeptides (nucleotide sequence SEQ ID NO:3; polypeptide sequence SEQ ID NO:4, Accession number M20165). An HSV recombinase includes an alkaline nuclease homologous to HSV-1 UL12 and a single-stranded DNA binding polypeptide homologous to HSV-1 ICP8, so long as the alkaline nuclease and single stranded DNA binding polypeptide together have polynucleotide strand exchange activity. "Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared. Falling within this generic term are the terms "ortholog", meaning a polynucleotide or polypeptide that is the functional equivalent of a polynucleotide or polypeptide in another species, and "paralog" meaning a functionally similar sequence when considered within the same species. Paralogs present in the same species or orthologs of the UL12 and ICP8 genes in other species can readily be identified without undue experimentation, by molecular biological techniques well known in the art. As used herein, UL12 refers to HSV-1 UL12 as well as its homologs and orthologs. Similarly, ICP8 refers to HSV-1 ICP8 as well as its homologs and orthologs.

As used herein, "percent homology" of two amino acid sequences or of two nucleic acids is determined using the algorithm of Karlin and Altschul (1990) *Proc. Natl. Acad. Sci., U.S.A.* 87: 2264–2268. Such an algorithm is incorporated into the NBLAST and XBLAST programs of Altschul et al. (1990) *J. Mol. Biol.* 215: 403–410. BLAST nucleotide searches are performed with the NBLAST program, score=100, wordlength 12, to obtain nucleotide sequences homologous to a nucleic acid molecule of the invention. BLAST protein searches are performed with the XBLAST program, score=50, wordlength=3, to obtain amino acid sequences homologous to a reference polypeptide (e.g., SEQ ID NO:2). To obtain gapped alignments for comparison purposes, Gapped BLAST is utilized as described in Altschul et al. (1997) *Nucleic Acids Res.* 25: 3389–3402. When utilizing BLAST and Gapped BLAST programs, the default parameters are typically used. (See http://www.ncbi.nlm.nih.gov)

The HSV recombinase includes polynucleotides that encode the UL12 and ICP8 polypeptides or full-length protein that contain substitutions, insertions, or deletions into the polypeptide backbone. Related polypeptides are aligned with UL12 and ICP8 by assigning degrees of homology to various deletions, substitutions and other modifications. Homology can be determined along the entire polypeptide or polynucleotide, or along subsets of contiguous residues. The percent identity is the percentage of amino acids or nucleotides that are identical when the two sequences are compared. The percent similarity is the percentage of amino acids or nucleotides that are chemically similar when the two sequences are compared. UL12 or ICP8 and homologous polypeptides are preferably greater than or equal to about 75%, preferably greater than or equal to about 80%, more preferably greater than or equal to about 90% or most preferably greater than or equal to about 95% identical.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria.

Reference herein to either the nucleotide or amino acid sequence of UL12 and ICP8 also includes reference to naturally occurring variants of these sequences. Nonnaturally occurring variants that differ from SEQ ID NOs:2 and 4 and retain biological function are also included herein. Preferably the variants comprise those polypeptides having conservative amino acid changes, i.e., changes of similarly charged or uncharged amino acids. Genetically encoded amino acids are generally divided into four families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cystine, serine, threonine, tyrosine). Phenylalanine, tryptophan, and tyrosine are sometimes classified jointly as aromatic amino acids. As each member of a family has similar physical and chemical properties as the other members of the same family, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule. Whether an amino acid change results in a functional polypeptide can readily be determined by assaying the properties of the UL12 and ICP8 polypeptide derivatives.

Reference to UL12 or ICP8 also refers to polypeptide derivatives of UL12 and ICP8. As used herein, "polypeptide derivatives" include those polypeptides differing in length from a naturally-occurring UL12 and ICP8 and comprising about five or more amino acids in the same primary order as is found in UL12 and ICP8. Polypeptides having substantially the same amino acid sequence as UL12 and ICP8 but possessing minor amino acid substitutions that do not substantially affect the ability of UL12 and ICP8 polypeptide derivatives to interact with UL12- and ICP8-specific molecules, respectively, such as antibodies, are within the definition of UL12 and ICP8 polypeptide derivatives. Polypeptide derivatives also include glycosylated forms, aggregative conjugates with other molecules and covalent conjugates with unrelated chemical moieties.

The UL12 and ICP8 polypeptides or their homologs can be expressed in a suitable in vitro overexpression system, purified, and mixed to form an active recombinase. Alternatively, the UL12 and ICP8 genes or their homologs can be expressed in vectors suitable for in vivo expression such as, for example, viral expression systems. In this case, the active recombinase would be formed when the two proteins are expressed in vivo. In yet another alternative, one of UL12 and ICP8 can be purified and the other expressed from a vector suitable for its expression in vivo.

The UL12 and ICP8 polynucleotides can be inserted into a recombinant expression vector or vectors. The term "recombinant expression vector" refers to a plasmid, virus, or other means known in the art that has been manipulated by insertion or incorporation of the UL12 or ICP8 genetic sequence. The term "plasmids" generally is designated herein by a lower case p preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors may be transformed into a suitable host cell to form a host cell vector system for the production of a polypeptide.

The UL12 and ICP8 polynucleotides can be inserted into a vector adapted for expression in a bacterial, yeast, insect, amphibian, or mammalian cell that further comprises the regulatory elements necessary for expression of the nucleic acid molecule in the bacterial, yeast, insect, amphibian, or mammalian cell operatively linked to the nucleic acid molecule encoding UL12 or ICP8. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., atg) in front of a protein-encoding gene, splicing signals for introns (if introns are present), maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al. (1987) *Methods in Enzymology* 153: 516–544).

Suitable vectors for insect cell lines (i.e., SF9 and SF21 cells) include baculovirus vectors. Human cells are preferred mammalian cells.

Transformation of a host cell with an expression vector or other DNA may be carried out by conventional techniques as are well known to those skilled in the art. By "transformation" is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell. By "transformed cell" or "host cell" is meant a cell (e.g., prokaryotic or eukaryotic) into which (or into an ancestor of which) has been introduced, by means of recombinant DNA techniques, a DNA molecule encoding a polypeptide of the invention (i.e., a UL12 and/or ICP8 polypeptide), or fragment thereof.

When the host is a eukaryote, such methods of transfection with DNA include calcium phosphate co-precipitates, mechanical procedures such as microinjection, electroporation, insertion of a plasmid encased in liposomes, or virus vectors, as well as others known in the art, may be used. Eukaryotic cells can also be cotransfected with DNA sequences encoding a polypeptide of this disclosure, and a second foreign DNA molecule encoding a selectable phenotype, such as the herpes simplex thymidine kinase gene. Suitable markers include, for example, neomycin and hygromycin, and the like, that can be taken up by mammalian cells. Resistance to the marker can be conferred by the neomycin gene or the hygromycin gene, for example, when the gene has a suitable eukaryotic promoter. Another method is to use a eukaryotic viral vector, such as simian virus 40 (SV40), adenovirus, or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*) or may be a mammalian cell, including a human cell.

Mammalian cell systems that utilize recombinant viruses or viral elements to direct expression may be engineered. For example, when using adenovirus expression vectors, the nucleic acid sequences encoding a foreign protein may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome will result in a recombinant virus that is viable and capable of expressing the UL12 or ICP8 polypeptide in infected hosts (e.g., Logan & Shenk (1984) *Proc. Natl. Acad. Sci. U.S.A.* 81:3655–3659).

For long-term, high-yield production of recombinant polypeptides, stable expression is preferred. Rather than using expression vectors that contain viral origins of replication, host cells can be transformed with the cDNA encoding a UL12 or ICP8 fusion polypeptide controlled by appropriate expression control elements (e.g., promoter sequences, enhancer sequences, transcription terminators, polyadenylation sites, etc.), and a selectable marker. The selectable marker in the recombinant plasmid confers resistance to the selection and allows cells to stably integrate the plasmid into their chromosomes and grow to form foci, which in turn can be cloned and expanded into cell lines. For example, following the introduction of foreign DNA, engineered cells may be allowed to grow for 1 to 2 days in an enriched media, and then switched to a selective media. A number of selection systems may be used, including but not limited to the herpes simplex virus thymidine kinase (Wigler et al. (1977) *Cell* 11: 233), hypoxanthine-guanine phosphoribosyltransferase (Szybalska & Szybalski (1962) *Proc. Natl. Sci. U.S.A.* 48: 2026), and adenine phosphoribosyltransferase (Lowy et al. (1980) *Cell* 22: 817) genes can be employed in tk, hgprt or aprt cells respectively. An alternative selection system is G418 resistance using geneticin.

The UL12 and ICP8 polypeptides can also be designed to provide additional sequences, such as, for example, the addition of coding sequences for added C-terminal or N-terminal amino acids that would facilitate purification by trapping on columns or use of antibodies. Such tags include, for example, histidine-rich tags that allow purification of polypeptides on Nickel columns. Such gene modification techniques and suitable additional sequences are well known in the molecular biology arts.

UL12 and ICP8 proteins, polypeptides, or polypeptide derivatives can be purified by methods known in the art. These methods include, but are not limited to, size exclusion chromatography, ammonium sulfate fractionation, ion exchange chromatography, affinity chromatography, crystallization, electrofocusing, preparative gel electrophoresis, and combinations comprising one or more of the foregoing methods. Preferably, purification is according to methods known to those of skill in the art that will result in a preparation of UL12 or ICP8 substantially free from other polypeptides and from carbohydrates, lipids, or subcellular organelles. A preparation of isolated and purified UL12 or ICP8 is about 50% to about 99.9% pure, with greater than or equal to about 80%, preferred, greater than or equal to about 85% purity more preferred, greater than or equal to about 90% purity more preferred, and greater than or equal to about 95% especially preferred. Purity may be assessed by means known in the art, such as SDS-polyacrylamide gel electrophoresis.

In an active recombinase, UL12 and ICP8 or their homologs are present in a ratio sufficient to promote strand exchange reactions in DNA. UL12 and ICP8 can be present in a ratio of about 1:500, preferably about 1:250, more preferably about 1:125. In certain circumstances, UL12 and ICP8 can be present at a ratio of about 1:1.

The invention also includes methods of use of the HSV recombinase. In one embodiment, the invention includes methods of cloning and gene transfer. Such methods can be performed in vitro or in a host cell. The method comprises contacting an HSV recombinase, a donor polynucleotide, and a target polynucleotide under conditions sufficient to promote homologous recombination.

When an in vitro system is used, the appropriate buffers and reagents for the cloning and gene transfer reactions can be added. Such buffers and reagents are those sufficient to promote homologous recombination. Buffers include, for example, Tris, Hepes, and glycine. Buffers are used to maintain the pH at a suitable range for HSV recombinase activity. A suitable pH range is, for example, 6.0 to 9.5, preferably 7.5 to 9.0. Additional reagents can also be added. Salts of monovalent and divalent metals such as, for example, sodium chloride, magnesium chloride, manganese chloride, and combinations comprising one or more of the foregoing salts can be added. Also, dithiothretol (DTT), beta-mercaptoethanol and other reagents known to stabilize the activity of proteins and enzymes may be added.

When used, the host cell is of a type suitable for expression of an HSV recombinase. The host cell can comprise, for example, an insect cell, an amphibian cell, or a mammalian cell. Suitable mammalian cells, for example, comprise cells from mouse, human, monkey, and the like. Suitable mammalian cell lines include, for example, CHO, VERO, BHK, HeLa, COS, Md.CK, 293, 3T3, W138 cells, and the like.

The HSV recombinase can be introduced into the in vitro system or host cell by many methods. One or more components of the HSV recombinase can be delivered, for example, as purified polypeptides. If introduced as purified polypeptides, an HSV alkaline nuclease and/or single-stranded DNA binding polypeptide can be purified by methods as described previously herein. If a host cell is used, entry of the purified polypeptides into a host cell can be mediated, for example, by a liposmal delivery method.

Alternatively, if a host cell is used, an HSV alkaline nuclease and/or single-stranded DNA binding polypeptide can be constitutively or inducibly expressed in the host cell using a DNA vector suitable for the polypeptide expression in the particular host cell. If the host cell is an SF9 cell, for example, the DNA vector can be a baculovirus vector. If the host cell is a mammalian cell, the DNA vector can be a vaccinia virus vector, an adenovirus vector, or the like. Expression of the HSV recombinase in the host cell can be constitutive or inducible (i.e., regulated by a second nucleic acid sequence). Promoters and enhancers (i.e., DNA sequences that regulate protein expression) are known in the art. Promoters that can be used to regulate HSV recombinase expression include, for example, the SV40 early promoter region, the cytomegalovirus promoter, the Moloney leukemia virus promoter, the promoter in the 3' long terminal repeat of the Rous sarcoma virus, the herpes thymidine kinase promoter, the regulatory sequences of the metallothionein gene, and the like. In addition, polynucleotides encoding the alkaline nuclease and the single stranded DNA binding protein can be present on the same or different vectors.

Expression vectors comprising the HSV recombinase can be transfected into a host cell by means known in the art. Such methods include, for example, electroporation, microinjection, complexing the DNA with a lipid layer as in *PNAS* (1987) 84: 7413, in a dendrimer as in *Bioconjugate Chem* (1993) 4: 85–93, and the like.

The donor polynucleotide comprises a first donor homology region at a first end, a second donor homology region at a second end, and an exogenous sequence therebetween. The donor polynucleotide may be prepared by, for example, chemical synthesis of oligonucleotides; nick-translation of a double-stranded DNA template; the polymerase chain reaction; a cloning vector harboring a polynucleotide of interest (i.e. a cloned cDNA, genomic DNA, or portion thereof) such as plasmids, cosmids, phagemids, yeast artificial chromosomes (YACs); bacteriophage DNA; other viral DNA; replication intermediates; restriction fragments comprising at least one of the foregoing polynucleotides; as well as other sources of polynucleotides having a desired nucleotide sequence. The donor polynucleotide can be double-stranded or single-stranded, preferably comprising two complementary single-stranded DNAs.

The donor polynucleotide can comprise greater than or equal to about 10 nucleotides, preferably greater than or equal to about 100 nucleotides, and more preferably greater than or equal to about 250 nucleotides. The donor polynucleotide can comprise less than or equal to about 400,000 nucleotides, preferably less than or equal to about 50,000 nucleotides, preferably less than or equal to about 20,000 nucleotides, preferably less than or equal to about 10,000 nucleotides, and most preferably less than or equal to about 2,000 nucleotides.

The donor polynucleotide comprises a first donor homology region at a first end and a second donor homology region at a second end. The first and second donor homology regions enable the formation of a heteroduplex joint during the process of homologous recombination. The length of the first and second donor homology regions can be selected on the basis of the sequence homology and complexity of the donor polynucleotide and the target polynucleotide. The first and second donor homology regions can comprise greater than or equal to about 15 nucleotides, preferably greater than or equal to about 25 nucleotides, and more preferably greater than or equal to about 100 nucleotides. The first and second donor homology regions can comprise less than or equal to about 2,000 nucleotides, preferably less than or equal to about 1,000 nucleotides, and more preferably less than or equal to about 500 nucleotides.

The donor polynucleotide also comprises an exogenous sequence between the first and second donor homology regions. The exogenous sequence comprises the sequence to be inserted into the target polynucleotide during a homologous recombination event. The exogenous sequence can comprise, for example, a gene, a fragment of a gene, a cDNA, a genomic DNA, and the like. The exogenous sequence can comprise a sequence that is not present in the target polynucleotide. Alternatively, the exogenous sequence can comprise a sequence with a single nucleotide mismatch as compared to the target polynucleotide, a sequence with several mismatches, or may span up to several kilobases of nonhomologous sequence. Nonhomologous portions in the exogenous sequence as compared to the target polynucleotide can be used to make insertion, deletions, substitutions (single or multiple), and or replacements in the target DNA.

When the method is performed in a host cell, the donor polynucleotide can be transfected into the cell by means known in the art. Such means include, for example, electroporation, microinjection, complexing the DNA with a lipid layer, in a dendrimer, and the like.

The target polynucleotide comprises a first target homology region at a first end, a second target homology region at a second end, and an endogenous sequence therebetween. The target polynucleotide may be prepared by, for example, chemical synthesis of oligonucleotides, nick-translation of a double-stranded DNA template; the polymerase chain reaction; and the like. The target polynucleotide may comprise a chromosome; a cloning vector harboring a polynucleotide of interest (i.e. a cloned cDNA, genomic DNA, or portion thereof) such as plasmids, cosmids, phagemids, yeast artificial chromosomes (YACs); bacteriophage DNA; other viral DNA; replication intermediates; restriction fragments comprising at least one of the foregoing polynucleotides; as well as other sources of polynucleotides having a desired nucleotide sequence. The target polynucleotide can be double-stranded or single-stranded, preferably comprising two complementary single-stranded DNAs.

The target polynucleotide can comprise greater than or equal to about 10 nucleotides, preferably greater than or equal to about 100 nucleotides, and more preferably greater than or equal to about 250 nucleotides. The target polynucleotide can comprise less than or equal to about 400,000 nucleotides, preferably less than or equal to about 50,000 nucleotides, preferably less than or equal to about 20,000 nucleotides, preferably less than or equal to about 10,000 nucleotides and most preferably less than or equal to about 2,000 nucleotides. In some cases, the target polynucleotide may comprise an entire chromosome.

The target polynucleotide comprises a first target homology region at a first end and a second target homology region at a second end. The length of the first and second target homology regions can be selected on the basis of the sequence homology and complexity of the donor polynucleotide and the target polynucleotide. The first and second target homology regions can comprise greater than or equal to about 15 nucleotides, preferably greater than or equal to about 25 nucleotides, and more preferably greater than or equal to about 100 nucleotides. The first and second target homology regions can comprise less than or equal to about 2,000 nucleotides, preferably less than or equal to about 1,000 nucleotides, and more preferably less than or equal to about 500 nucleotides.

The first donor homology region and the first target homology region can be substantially homologous. Similarly, the second donor homology region and the second target homology region can be substantially homologous. By substantially homologous, it is meant that the sequences have greater than or equal to about 70% sequence identity or complementarity, preferably greater than or equal to about 85% sequence identity or complementarity, and more preferably greater than or equal to about 90% sequence identity or complementarity. The substantial homology of the homology regions can facilitate heteroduplex formation during homologous recombination.

The target DNA comprises an endogenous sequence. The endogenous sequence is the sequence to be replaced during homologous recombination. The endogenous sequence can be homologous to the exogenous sequence or can be a nonhomologous sequence. The endogenous sequence can, for example, be a polylinker region. Alternatively, the endogenous sequence can comprise a gene of interest. The endogenous sequence can also comprise regulatory sequences for gene transcription and translation.

When the cloning method is performed in a host cell, the target polynucleotide can be transfected into the cell by means known in the art. Such means include, for example, electroporation, microinjection, complexing the DNA with a lipid layer, in a dendrimer, and the like.

In another embodiment, kits that facilitate the use of homologous recombination for use in cloning and subcloning are provided. The kits comprises an HSV recombinase; a target polynucleotide useful for cloning, the target polynucleotide comprising a first target homology region at a first end, a second target homology region at a second end, and an endogenous sequence therebetween as described above. The HSV recombinase can comprise purified alkaline nuclease and single stranded DNA binding polypeptide, vectors suitable for the expression of the HSV alkaline nuclease and single stranded DNA binding protein, or a combination of purified proteins and expression vectors. The homologous recombination reaction can be performed in vitro. Alternatively, a host cell suitable for homologous recombination can be provided. The host cell can further comprise expression vector(s) for the production of an HSV alkaline nuclease and/or single-stranded DNA binding protein.

In another embodiment, the HSV recombinase can be used in methods of treating cells and organisms such as, for example, somatic gene therapy applications. Somatic gene therapy can be defined as the ability to program the expression of foreign genes in non-germ line (i.e., non-sperm and egg) cells of an animal or human.

Methods of gene therapy can be divided into two categories: ex vivo and in vivo. Ex vivo gene therapy involves the removal of cells from a host organism, introduction of a foreign gene into those cells in the laboratory, and reimplantation or transplantation of the genetically modified cells back into a recipient host. In contrast, in vivo gene therapy involves the introduction of a foreign gene directly into cells of a recipient host without the need for prior removal of those cells from the organism. In vivo gene therapy can make use of infectious vectors such as retroviral vectors that include the HSV recombinase.

There are a number of requirements that should be met by a method of gene therapy before it can be considered potentially useful for human therapeutics. First, one should develop an efficient method for introducing the foreign gene into the appropriate host cell. Secondly, it would be preferable to develop systems that program expression of the gene only in the appropriate host cell type, thus preventing expression of the foreign gene in an inappropriate cell. Finally, and most importantly when considering human gene therapy, the technique should have a minimal risk of mutating the host cells and of causing a persistent infection of the host organism, a particularly important worry when using virus vectors to introduce foreign genes into host cells. Somatic gene therapy is described in detail in Ledley, F., (1991) *Human Gene Therapy* 2: 77–83, and Ledley, F., (1996) *Pharmaceutical Research* 13: 1595–1613.

Gene therapy can, for example, be used to correct defects associated with human diseases of genetic origin including, for example, diabetes mellitus, cystic fibrosis, thalassaemias, sickle cell anemia, Franconi's anemia, retinitis pigmentosa, Xeroderma pigmentosa, Duchenne's muscular dystrophy, Tay-Sach's disease, and the like. Gene therapy can also be used to alter the DNA sequences of cells with other genetic defects such as cancer. The method can be used for a gene where the normal DNA sequence is known or where a normal, wild-type DNA fragment is available to provide functional DNA sequences. Other DNAs may be used so as to produce an alteration in cellular DNA with an associated change in the gene function.

Sickle cell anemia is an example of a disease that can be targeted by gene therapy. Classical sickle cell anemia afflicts as many as 1 in 64 black people in Africa and from 1 in 200 to 1 in 400 black people in the United States. The disease is caused by an A to T transversion in the sixth codon of the human beta-globin gene resulting in a Glu to Val substitution in the protein. Phenotypically, there is a polymerization of the hemoglobin that results in many pathologies that ultimately lead to death of the individual. Numerous therapies lead to amelioration of the effects of the mutation, however, sickle cell anemia would be a good candidate for gene therapy.

Diabetes mellitus is a chronic disease causing kidney failure, heart disease, stroke and blindness. In diabetes mellitus, the pancreas no longer produces enough insulin or cells stop responding to the insulin produced such that glucose cannot be absorbed by the cells of the body. Standard treatments include dietary changes, oral medications, and daily injections of insulin. Genetically modified pancreatic beta cells could be used to treat diabetes patients.

Gene therapy can also be used in the treatment of infectious disease. The exogenous sequence that is added can contain mutations that inactivate a pathogen by introducing mutant sequences into essential genes of the genome of the pathogen. Retroviral pathogens such as HIV are candidates for gene therapy using homologous recombination. These viruses rely on the integration of the proviral DNA into the cellular genome as a part of their replicative cycle. The proviral DNA thus can be a target for the added exogenous DNA. At least one exogenous DNA with an inactivating mutation in an essential viral gene can be used to disrupt the integrity of the viral genome and the ability of the virus to replicate.

The method of gene therapy comprises delivering into a eukaryotic host cell an HSV recombinase and a donor polynucleotide as described above for the gene cloning method. The eukaryotic host cell can comprise the target polynucleotide. Alternatively, the target polynucleotide can also be delivered to the eukaryotic host cell. Gene therapy can be either in vivo or ex vivo.

The HSV recombinase (an HSV alkaline nuclease and/or single-stranded DNA binding polypeptide) can be delivered, for example, as purified polypeptides. If introduced as purified polypeptides, the HSV recombinase can be purified by methods as described previously herein. Entry of the purified polypeptides into a host cell can be mediated, for example, by a liposmal delivery method.

Alternatively, the HSV recombinase (an HSV alkaline nuclease and/or single-stranded DNA binding polypeptide) can be expressed in the host cell using a DNA vector suitable for the particular host cell. Suitable vectors for the expression of the HSV recombinase in a host cell are those vectors suitable for gene therapy applications and that allow for protein expression. The polynucleotides encoding the alkaline nuclease and the single stranded DNA binding protein can be present on the same or different vectors. The HSV recombinase can be introduced into the cell on the same or on a different vector than the donor DNA.

The donor polynucleotide comprises a first donor homology region at a first end, a second donor homology region at a second end, and an exogenous sequence therebetween. The length of the first and second donor homology regions can be selected on the basis of the sequence homology and complexity of the donor polynucleotide and the target polynucleotide. The first and second donor homology regions can comprise greater than or equal to about 15 nucleotides, preferably greater than or equal to about 25 nucleotides, and more preferably greater than or equal to about 100 nucleotides. The first and second donor homology regions can comprise less than or equal to about 2,000 nucleotides, preferably less than or equal to about 1,000 nucleotides, and more preferably less than or equal to about 500 nucleotides.

The exogenous sequence of the donor polynucleotide can be a polynucleotide that encodes an endogenous DNA sequence in the organism being treated with gene therapy. As used herein, endogenous gene refers to the gene to be treated (i.e., targeted) with gene therapy. The endogenous (i.e., targeted) DNA sequence can be, for example, a gene that encodes a polypeptide such as an enzyme, a structural protein, a soluble protein, and the like; or a regulatory DNA sequence such as promoters, transcriptional and translational start sequences, repetitive sequences, and the like.

The exogenous sequence of the donor DNA can be modified in many ways, including gene disruptions and alterations. The endogenous gene may be disrupted in a variety of ways. As used herein, disruption means a change in the coding sequence of a gene that results in an alteration in the transcription or translation of the gene. In general, disruption can occur by the insertion, deletion, or frameshifting of nucleotides. Alterations of an endogenous gene can include nucleotide substitutions that affect either the regulatory sequences, coding sequences, or noncoding sequences (such as, for example, introns) of the gene.

The exogenous sequence can comprise an insertion sequence. The term insertion sequence refers to one or more nucleotides that are inserted into an endogenous gene to disrupt it. Insertion sequences can be as short as about one nucleotide to as long as about the length of a gene. For insertion less than the length of a gene, preferred insertions comprise greater than or equal to about 1 nucleotide, with about 1 to about 50 nucleotides preferred, and about 10 to about 25 nucleotides more preferred. The insertion may comprise a polylinker sequence that is greater than or equal to about 1 nucleotide, with about 1 to about 50 nucleotides preferred, and about 10 to about 25 nucleotides more preferred.

The insertion sequence can comprise a gene that not only disrupts the endogenous gene, but can also result in the production of a new gene product. Thus, the disruption of the endogenous gene can be done in a manner to allow transcription and translation of the exogenous sequence of the donor polynucleotide. An insertion sequence that encodes a gene can comprise, for example, about 50 to about 5,000 base pairs of cDNA or about 5,000 to about 50,000 base pairs of genomic DNA. The insertion sequence in the exogenous DNA can be inserted into the endogenous DNA sequence in such a manner as to utilize endogenous regulatory sequences, including, but not limited to, promoters, enhancers, and the like. Alternatively, the insertion sequence of the exogenous sequence can include at least one regulatory sequence such as promoters, enhancers, and the like.

The insertion sequence can thus be a gene that encodes a polypeptide of therapeutic interest. The insertion sequence can comprise a sequence that encodes a polypeptide with biological activity, for example, a gene encoding an enzyme that has enzymatic activity. As used herein, a biologically active polypeptide is a polypeptide, that when expressed in a host eukaryotic cell, is in a form expected to result in its biological function. Alternatively, the target sequence can encode other polypeptides, such as, for example, antibodies or structural proteins.

The insertion sequence can be a modified or variant gene, i.e., a sequence that contains a mutation from the endogenous sequence. As such, the modified gene can contain a mutation that restores activity to an endogenous gene that produces a polypeptide lacking activity. Alternatively, the modified gene can comprise a mutation that increases or otherwise improves that activity of an endogenous gene product.

Alternatively, the insertion sequence can comprise a reporter gene. Suitable reporter genes are those that encode detectable proteins such as luciferase; beta-galactosidase; the fluorescent proteins such as green fluorescent protein (GFP), blue fluorescent protein (BFP), yellow fluorescent protein (YFP) and red fluorescent protein (RFP); and the like.

The exogenous sequence of the donor DNA can comprise a deletion. As used herein, deletion refers to removal of a portion of an endogenous gene. Deletions can be about 1 to about 100 nucleotides, with about 1 to about 25 nucleotides preferred, although in some cases, deletions can be much larger and effectively result in the removal of a gene and/or its regulatory sequences. Deletions may be combined with insertions or other modified sequences.

The endogenous gene can also be altered by nucleotide substitutions, insertions, deletions that do not eliminate the biological function of a gene product, but rather alter it. The exogenous sequence can thus be used to alter gene function. For example, defective genes may be modified to produce an active gene product. Alternatively, defective regulatory sequences can be modified to produce active regulatory sequences.

In some cases, it may be desirable to add exogenous DNA sequences, such as exogenous genes or extra copies of endogenous genes, to an organism. Cases where adding an exogenous gene include to alleviate disease states, for example by adding a wild type gene or to add copies of a therapeutic gene; to add therapeutic genes such as tumor suppressor genes (e.g., p53, Rb1, Wt1, NF1, NF2, and APC) or other therapeutic genes; or to produce gene products suitable for polypeptide production in vivo.

When the endogenous gene is a structural gene, amino acid changes can be made as is known in the art. Substitutions, deletions, insertions or combinations thereof can be used to arrive at a modified gene product. Changes can be done with a few amino acids to minimally change the resulting polypeptide. Larger changes, however, can be made depending on the circumstances.

The target polynucleotide comprises a first target homology region at a first end, a second target homology region at a second end, and an endogenous sequence therebetween. The length of the first and second target homology regions can be selected on the basis of the sequence homology and complexity of the donor polynucleotide and the target polynucleotide. The first and second target homology regions can comprise greater than or equal to about 15 nucleotides, preferably greater than or equal to about 25 nucleotides, and more preferably greater than or equal to about 100 nucleotides. The first and second target homology regions can comprise less than or equal to about 2000 nucleotides, preferably less than or equal to about 1000 nucleotides, and more preferably less than or equal to about 500 nucleotides.

The first donor homology region and the first target homology region can be substantially homologous. Similarly, the second donor homology region and the second target homology region can be substantially homologous. By substantially similar, it is meant that the sequences have greater than or equal to about 70% sequence identity or complementarity, preferably greater than or equal to about 85% sequence identity or complementarity, and more preferably greater than or equal to about 90% sequence identity or complementarity. The substantial homology of the homology regions can facilitate heteroduplex formation during homologous recombination.

For ex vivo gene therapy applications, the target polynucleotide can be isolated from a DNA sample such as genomic DNA, cDNA or mitochondrial DNA. The target polynucleotide can be isolated from a biological sample from a human or animal. The biological sample can comprise, for example, whole blood plasma, serum, skin, saliva, urine, lymph fluid, cells obtained from a biopsy aspirate, tissue culture cells, or media. The target polynucleotide alternatively is isolated from non-biological samples such as food or water. Methods of preparation and sequencing of DNA samples are well known in the art. Alternatively, the cell to be treated with ex vivo gene therapy may comprise the target polynucleotide.

For in vivo gene therapy applications, the organism to be treated with gene therapy can comprise the target polynucleotide in its cells.

In both in vivo and ex vivo gene therapy, the HSV recombinase and the donor polynucleotide can be inserted into cells using vectors that include, but are not limited to adenovirus, adenoma-associated virus, retrovirus vectors, and the like, in addition to other particles that introduce DNA into cells, such as liposomes. More complete descriptions of gene therapy vectors, especially retroviral vectors are contained in U.S. Pat. Nos. 6,190,907; 6,140,111; 6,096,534; 5,741,486; and 5,714,353 and in EP 0827545 which are incorporated herein by reference. Alternatively, techniques such as those described above may be utilized for the introduction of exogenous gene sequences into cells. For ex vivo gene therapy applications, the target polynucleotide can be introduced by similar methods.

The donor DNA may be conjugated, either covalently or noncovalently, to a cell-uptake component by means well known in the art. The cell-uptake component can be made by incubating the donor polynucleotide with at least one lipid species and at least one protein species to form lipid-protein-polynucleotide complexes. Lipid vesicles made according to WO91/17424 and/or cationic lipidization (WO91/16024) or other forms of polynucleotide administration (EP 465,529) can be used.

In ex vivo gene therapy, cells can be removed from an organism, modified, and then returned to the organism. Cells can be removed from a variety of locations including, for example, from a selected tumor or from an affected organ. In addition, the cells can be non-tumorigenic cells, for example, dermal fibroblasts or peripheral blood leukocytes. If desired, particular fractions of cells such as a T cell subset or stem cells can also be specifically removed from the blood (see, for example, PCT WO 91/16116). The HSV recombinase and the donor polynucleotide can then be contacted with the removed cells utilizing any of the above-described techniques, followed by the return of the cells to the organism, preferably to or within the vicinity of a tumor. The above-described methods can additionally comprise the steps of depleting fibroblasts or other non-contaminating tumor cells subsequent to removing tumor cells from a human, and/or the step of inactivating the cells, for example, by irradiation.

For in vivo gene therapy, the HSV recombinase and the donor polynucleotide can be administered by means known in the art and can further comprise a pharmaceutically acceptable carrier. Pharmaceutically acceptable carriers include, but are not limited to, large, slowly metabolized macromolecules such as polypeptides, polysaccharides, polylactic acids, polyglycolic acids, polymeric amino acids, amino acid copolymers, inactive virus particles, and the like. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, or EP 524,968 B1, can also be used as a carrier for the therapeutic composition.

The HSV recombinase and donor polynucleotide can be prepared as an injectable liquid solution or suspension. However solid forms suitable for solution in, or suspension in, liquid vehicles prior to injection can also be prepared. The composition can also be formulated into an enteric-coated tablet or gel capsule according to known methods in the art, such as those described in U.S. Pat. No. 4,853,230 and EP 225,189. Administration of the HSV recombinase and the donor polynucleotide can include local or systemic administration, including injection, oral administration, particle gun, catheterized administration, topical administration, and the like.

Receptor-mediated targeted delivery of therapeutic compositions containing the HSV recombinase to specific tissues can also be used. Receptor-mediated DNA delivery techniques are described in, for example, Findeis et al. (1993) *Trends in Biotechnol.* 11: 202–05; Chiou et al. (1994) Gene Therapeutics: Methods and applications of Direct Gene Transfer (J. A. Wolff, ed.); Wu & Wu (1988) *J. Biol. Chem.* 263: 621–24; Wu et al. (1994), *J. Biol. Chem.* 269: 542–46; Zenke et al. (1990) *Proc. Natl. Acad. Sci. U.S.A.* 87: 3655–59; Wu et al. (1991) *J. Biol. Chem.* 266: 338–42.

In another embodiment, similar methods to the previously described ex vivo gene therapy methods can be used to produced modified host cells. The method of making modified host cells comprises delivering into a eukaryotic host cell an HSV recombinase and a donor polynucleotide as described above for the gene therapy method. The eukaryotic host cell can comprise the target polynucleotide. Alternatively, the target polynucleotide can also be delivered to the eukaryotic host cell.

As with the gene therapy method, the donor polynucleotide can comprise an insertion sequence. The insertion sequence can be a modified or variant gene, i.e., a sequence that contains a mutation from the endogenous sequence. As such, the modified gene can contain a mutation that restores activity to an endogenous gene that produces a polypeptide lacking activity. Alternatively, the modified gene can comprise a mutation that increases or otherwise improves that activity of an endogenous gene product. Alternatively, the insertion sequence can comprise, for example, a reporter gene, a modified endogenous gene, a regulatory sequence or an exogenous gene.

Suitable host cells for making modified host cells include prokaryotic and eukaryotic cells, such as, for example, bacteria, yeast, amphibian, and mammalian cells. Mammalian cell lines include, for example, HeLa and VERO cells.

In another embodiment, the HSV recombinase can be used to make transgenic non-human animals. A transgenic non-human animal is one in which a heterologous DNA sequence is chromosomally integrated into the germ cells of the animal. The transgenic animal will also have the transgene integrated into the chromosomes of its somatic cells. Animals of species, including, but not limited to: amphibians, birds, mice, rats, rabbits, guinea pigs, pigs, micro-pigs, goats, and non-human primates, e.g., baboons, monkeys, chimpanzees, may be used to generate transgenic animals. Transgenic animals are particularly useful for the modification of disease alleles in a non-human animal. Sequence-modified non-human animals harboring a disease allele can provide useful models of human and veterinary diseases. Alternatively, homologous recombination can be used to provide non-human animals having disease alleles integrated into a non-human genome. Such animals can provide models of human genetic disease.

The method of producing transgenic animals comprises introducing at least the HSV recombinase and a donor polynucleotide into an embryonic stem cell, a fertilized zygote, and the like.

The HSV recombinase (an HSV alkaline nuclease and/or single-stranded DNA binding polypeptide) can be delivered, for example, as purified polypeptides. If introduced as purified polypeptides, the HSV recombinase can be purified by methods as described previously herein. Entry of the purified polypeptides into a host cell can be mediated, for example, by a liposmal delivery method.

Alternatively, the HSV recombinase (an HSV alkaline nuclease and/or single-stranded DNA binding polypeptide) can be expressed in the host cell using a DNA vector suitable for the particular host cell. Suitable vectors for the expression of the HSV recombinase in a host cell are those vectors that allow for polypeptide expression in embryonic stem cells and zygotes. The alkaline nuclease and the single stranded DNA binding protein can be expressed on the same or different vectors. The HSV recombinase can be introduced into the cell on the same or on a different vector than the donor DNA.

The donor polynucleotide comprises a first donor homology region at a first end, a second donor homology region at a second end, and an exogenous sequence therebetween. The exogenous sequence can comprise, for example a wild-type or a mutant sequence of a human gene.

The embryonic stem cell or zygote into which the donor polynucleotide is transferred will often comprise the target polynucleotide. The target polynucleotide comprises a first target homology region at a first end, a second target homology region at a second end, and an endogenous sequence therebetween. The length of the first and second homology regions can be selected on the basis of the sequence homology and complexity of the donor polynucleotide and the target polynucleotide. The first donor homology region and the first target homology region can be substantially homologous. Similarly, the second donor homology region and the second target homology region can be substantially similar. By substantially similar, it is meant that the sequences have greater than or equal to about 70% sequence identity or complementarity, preferably greater than or equal to about 85% sequence identity or complementarity, and more preferably greater than or equal to about 90% sequence identity or complementarity. The substantial homology of the homology regions can facilitate heteroduplex formation during homologous recombination.

Techniques known in the art may be used to introduce the polynucleotides into animals to produce the founder line of animals. Such techniques include, but are not limited to: pronuclear microinjection (U.S. Pat. No. 4,873,191); retrovirus mediated gene transfer into germ lines (Van der Putten et al. (1985) *Proc. Natl. Acad. Sci. USA* 82: 6148–6152); gene targeting in embryonic stem cells (Thompson et al. (1989) *Cell* 56: 313–321); electroporation of embryos (Lo (1983) *Mol. Cell Biol.* 3: 1803–1814); and sperm-mediated gene transfer (Lavitrano et al. (1989) *Cell* 57: 717–723). For a review of such techniques, see Gordon (1989) *Intl. Rev. Cytol.* 115: 171–229. Non-human zygotes can be used, for example, as described in U.S. Pat. No. 4,873,191.

Transgenic mammals can be prepared in a number of ways. In order to achieve stable inheritance of the extra or exogenous DNA fragment, the integration event should occur in a cell type that can give rise to functional germ cells. Two animal cell types that can form germ cells and into which DNA can be introduced readily are fertilized egg cells (i.e., zygotes) and embryonic stem cells. Embryonic stem (ES) cells can be returned from in vitro culture to a "host" embryo where they become incorporated into the developing animal and can give rise to transgenic cells in all tissues, including germ cells.

Embryonic stem cells can be used to make the transgenic non-human animal. The embryonic stem cells are used for gene targeting and the resulting mutant cells can be used to create transgenic animals and animals carrying null or "knock-out" mutations. A "knock-out" mutation refers to the disruption of a gene of interest with a complete loss of function. In such so-called "knock-out" animals, there is inactivation of the gene of interest or altered gene expression, such that the animals can be useful to study the function of the gene of interest, thus providing animals models of human disease, which are otherwise not readily available through spontaneous, chemical or irradiation mutagenesis. The embryonic stem cells that contain the gene of interest integrated into their genome by the HSV recombinase can be transmitted to the germline of an animal, such as a mouse, by injection into an early cleavage stage embryo (e.g., blastocyst), or by aggregation with two morulae to produce a chimera. "Chimera" is a term of art intended to mean an embryo containing cells or tissues with two or more genotypes. Chimeras carrying the mutated or donor nucleic acid sequence in their germ cells are then bred to produce transgenic offspring that are entirely derived from the embryonic stem cells that carry the mutation. Genetic markers such as coat color in mice can be used to distinguished chimeras and animals derived entirely from embryonic stem cells. Experimental techniques for obtaining, propagating, cloning and injecting embryonic stem cells are well known in the art. The animals carrying mutated germ cells are then bred to produce transgenic offspring.

Generally, the embryonic stem cells (ES cells) used to produce the transgenic or knock-out animals will be of the same species as the transgenic or knock-out animal to be generated. Thus for example, mouse embryonic stem cells will usually be used for generation of knock-out mice.

Embryonic stem cells (ES cells) are generated and maintained using methods well known to the skilled artisan such as those described by Doetschman et al. (1985) *J. Embryol. Exp. Mol. Biol.* 87:27–45. Many different lines of ES cells can be used, however, the line chosen is often selected for the ability of the cells to integrate into and become part of the germ line of a developing embryo so as to create germ line transmission of the knockout construct. Thus, ES cell lines believed to have this capability are particularly suitable for use herein. One mouse strain that can be used for production of ES cells, is the 129J strain. Another ES cell line is murine cell line D3 (American Type Culture Collection, catalog no. CKL 1934). Still another ES cell line is the WW6 cell line (Ioffe et al. (1995) *PNAS* 92:7357–7361). The cells are cultured and prepared for donor polynucleotide insertion using methods well known to the skilled artisan, such as those set forth by Robertson in: Teratocarcinomas and Embryonic Stem Cells: A Practical Approach, E.J. Robertson, ed. IRL Press, Washington, D.C. [1987]); by Bradley et al. (1986) *Current Topics in Devel. Biol.* 20: 357–371); and by Hogan et al. (Manipulating the Mouse Embryo: A Laboratory Manual, Cold Spring Harbor Laboratory Press, Cold Spring Harbor, N.Y. [1986]).

Another method for making transgenic animals is by zygote injection. This method is described, for example, in U.S. Pat. No. 4,736,866. The method involves injecting DNA into a fertilized egg, or zygote, and then allowing the egg to develop in a pseudo-pregnant mother. The zygote can be obtained using male and female animals of the same strain or from male and female animals of different strains. The transgenic animal that is born is called a founder, and it is bred to produce more animals with the same DNA insertion. In this method of making transgenic animals, the new DNA integrates into the genome by a homologous recombination event.

Generally, the DNA is injected into one of the pronuclei, usually the larger male pronucleus. The zygotes are then either transferred the same day, or cultured overnight to form 2-cell embryos and then transferred into the oviducts of pseudo-pregnant females. The animals born are screened for the presence of the desired integrated DNA. By a pseudo-pregnant female is intended a female in estrous who has mated with a vasectomized male; she is competent to receive embryos but does not contain any fertilized eggs. Pseudo-pregnant females are important for making transgenic animals since they serve as the surrogate mothers for embryos that have been injected with DNA or embryonic stem cells.

Transgenic animals such as mice, for example, may be used as test substrates for the identification of drugs, pharmaceuticals, therapies and interventions that can be used for the treatment of mammalian genetic disorders.

EXAMPLES

The invention is further illustrated by the following non-limiting examples.

Example 1

Purification of UL12 and ICP8

The UL12 and $UL12_{D340E}$ proteins were purified as described (Goldstein, J. N. and Weller, S. W. (1998) *Virology* 244: 442–57). Briefly, UL12 was purified from *Spodoptera frugiperda* (Sf21) cells infected with recombinant baculovirus AcAN for wild-type and AcAN(IIAla) and AcAN(IIGlu) for the mutant strains.

The $UL12_{D340E}$ mutant protein is essentially devoid of exonuclease activity. Cells were collected 50 hours after infection, pelleted, quick-frozen, and stored at −75° C. Cells were resuspended in 40 milliliters of buffer A (10 mM Tris-Cl pH 7.5, 1 mM $MgCl_2$, 0.5 mM dithiothretol, 80 mM KCl, 0.2% NP-40). Protease inhibitors (aprotinin, leupeptin, pepstatin A and phenylmethylsulfonyl fluoride) were added. Cells were incubated on ice for 10 minutes, then homogenized in a Dounce homogenizer. Nuclei were pelleted, and resuspended in 40 milliliters of Buffer A to extract nuclear proteins. The resuspension and pelleting was then repeated. The supernatants were combined to form an 80 mL cytosolic extract which was clarified by centrifugation. The extract was precipitated with 30% ammonium sulfate, and the precipitate removed by centrifugation. The resulting supernatant was then precipitated with 55% ammonium sulfate, incubated for 1 hour at 10° C., and centrifuged. The supernatant was removed and recentrifuged to collect all of the remaining precipitated protein. The pellets were resuspended in Buffer B (20 mM potassium phosphate, pH 8.0, 20% glycerol, 5 mM beta-mercaptoethanol) and dialyzed overnight against the same buffer. The dialyzed protein was centrifuged and then loaded on a Pharmacia HiLoad 16/10 SP-sepharose column equilibrated with Buffer B. The protein was eluted with a gradient of Buffer B to Buffer C (Buffer B but with 0.5 M potassium phosphate, pH 8.0). UL-12 fractions were pooled and concentrated. Following S-sepharose chromatography, the UL12 protein was further purified by gel filtration on a Superose-12 gel filtration column, or by a CHT-2 hydroxyapatite column. The UL12 protein has an activity of 0.2 nanograms DNA degraded/minute/nanograms protein, assayed as the release of acid-soluble counts from a $^3$H-*E. coli* DNA substrate under conditions optimal for UL12 nuclease activity (Goldstein, J. N. and Weller, S. W. (1998) *Virology* 244: 442–57). The nuclease activity of UL12 at standard strand exchange assay conditions (see below) was found to be 0.06 nanograms DNA degraded/minute/nanograms protein.

ICP8 was purified from *Spodoptera frugiperda* (Sf21) cells infected with recombinant baculovirus AcUL29 (Stow, N. D. (1992), *J. Gen. Virol.* 73: 313–21). Cells were collected 3 days after infection, pelleted, quick-frozen, and stored at −80° C. Three grams of frozen cells (wet weight) were resuspended in 30 milliliters of swelling buffer (10 mM Tris-Cl pH 7.5, 10 mM KCl, 1.5 mM $MgCl_2$) with 200 microliter of Sigma protease inhibitor cocktail. Cells were incubated on ice for 30 minutes, then homogenized in a Dounce homogenizer. Nuclei were pelleted, and resuspended in 20 milliliters of extraction buffer (swelling buffer with 1.2 M NaCl and protease inhibitors) to extract nuclear proteins. After a 40 minute incubation on ice, the mixture was centrifuged for 40 minutes (30,000 rpm at 4° C. in a Beckmann Ti70 rotor). The supernatant was dialyzed against 1.5 liter buffer A (20 mM Hepes pH 7.5, 10% glycerol (weight/volume), 0.1 mM NaCl, 0.1 mM EDTA, 1 mM DTT) for 16 hours at 4° C. During dialysis, a white precipitate formed which was removed by centrifugation and by filtration through a Millex-HV low protein binding 0.45 micrometer syringe filter (Millipore). The cleared extract was loaded onto an SP sepharose HiLoad 16/10 column (Pharmacia) using buffer A, and washed with three column volumes of buffer A. The protein was eluted using a linear gradient from 0.1–1M NaCl over 50 milliliters. ICP8 eluted at 0.3–0.4 M NaCl. The ICP8 peak fractions were pooled, and dialyzed against 1.5 liter of 20 mM Hepes pH 7.5, 10% glycerol (weight/volume), 0.5 mM EDTA, 0.5 mM DTT. The protein concentration was determined by the Bradford method and by UV absorbance at 280 nanometers (extinction coefficient 82,720 $M^{-1}cm^{-1}$). The protein concentration was 1.8 milligrams/milliliter (12.6 milligrams total yield) by both methods. The purity of the protein as estimated by Coomassie brilliant blue-stained gels was 95%. A nuclease assay (described below) was used to determine whether the purified ICP8 had any nuclease contaminants. The specific nuclease activity was found to be $8.6 \times 10^{-6}$ nanograms DNA released/minute/nanograms protein. Thus, the nuclease contamination of the ICP8 preparation was negligible.

Example 2

Strand Exchange Activity of UL12 and ICP8

An agarose gel-based strand exchange assay was used to test the ability of UL12 and ICP8 to promote strand exchange in vitro between linear double-stranded (ds) and circular single-stranded (ss) M13mp18 DNA. M13mp18 RF DNA was digested with BsrGI and gel purified. The purified DNA fragment was end-labeled by the exchange reaction, using T4 polynucleotide kinase, [α-$^{32}$P] ATP, and the exchange reaction buffer supplied by the manufacturer. The labeled fragment was then re-ligated with T4 DNA ligase, and then cleaved by PstI. The labeled 7.25 kilobase fragment (full-length M13) was gel-purified.

The double stranded DNA substrate was internally labeled at a single site, on both strands of the molecule. This 7.25 kilobase fragment had [$^{32}$P]-labeled nucleotides positioned 5.25 kilobases from the 5' end of the pairing strand, and 2 kilobases from the 5' end of the strand that would be displaced or degraded during strand exchange (see FIG. 1, top line). The asterisk marks the internal [$^{32}$P] label. Since UL12 is a 5' to 3' exonuclease, it was important to position the label at a distance from the 5' end. The internal location of the label also prevented its loss to any potential 3' to 5' exonuclease contaminants in the protein preparations. In addition, since each strand had only one labeled nucleotide, this simplified quantification of the products of the reaction.

The strand exchange reaction was carried out in a final volume of 20 microliters and consisted of: 100 nanograms of circular single-stranded M13mp18 DNA (2 nM), 100 nanograms linear [$^{32}$P]-labeled double-stranded M13mp18 (1 nM), 18.8 nanograms UL12 (13.9 nM), 4.5 micrograms ICP8 (1.75 µM), 20 mM Tris-Cl pH 7.5, 40 mM NaCl, 1 mM MgCl$_2$, and 1 mM DTT, or as indicated in the figure legends. The reaction mixture was incubated at 37° C. for the times indicated in the figure legends and stopped by adding 5 microliters of 5× stop buffer (50% glycerol, 50 mM EDTA, 1% SDS, 0.2% bromphenol blue). Samples were electrophoresed on a 1% agarose gel with 0.7 micrograms/milliliter ethidium bromide, using TAE buffer (0.04 M Tris-acetate, 0.001 M EDTA). Gels were dried and exposed to phosphorimager screens (NationalDiagnostics). The ImageQuant version 5.0 software package was used for quantification of the results.

Figure 2:
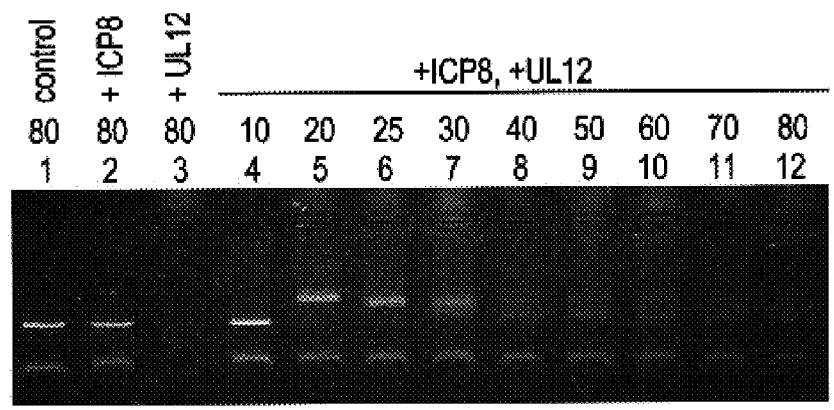
FIG. 2 shows the time course of joint molecule formation catalyzed by UL12 and ICP8.
Figure 3:
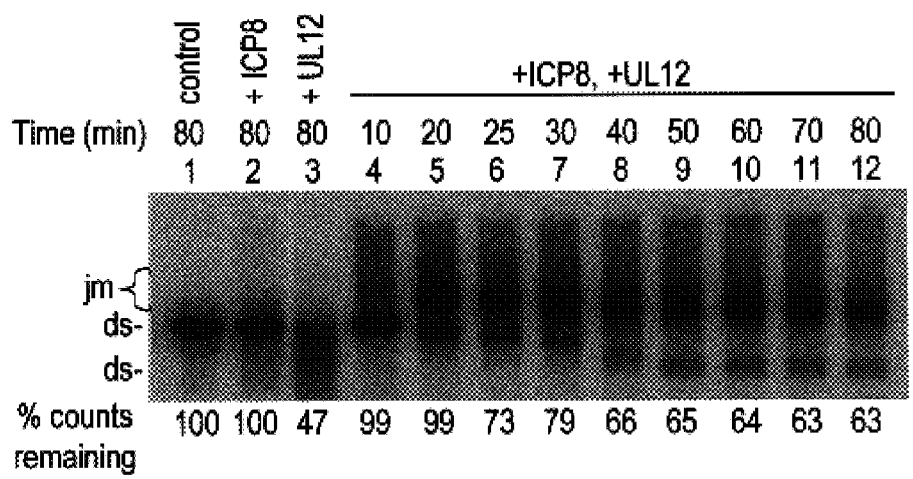
FIG. 3 is a phosphorimage of the experiment shown in FIG. 2.

Strand exchange catalyzed by UL12 and ICP8 is shown in FIGS. 2 and 3. Strand exchange reactions were carried out using the [$^{32}$P]-labeled linear M13 dsDNA (double-stranded DNA) and unlabeled circular M13 ssDNA (single-stranded DNA) substrates. FIG. 2 is a photograph of an ethidium bromide stained agarose gel. FIG. 3 is a phosphorimage of the same experiment. The percent radioactivity remaining in each lane, compared to the control lane, is indicated. Incubations were at 37° C. for the times indicated. Lane 1 is a control reaction with no proteins added; lane 2 is a strand exchange with ICP8 alone; lane 3 is a strand exchange with UL12 alone; lanes 4–12, are strand exchange by UL12 and ICP8. Jm, joint molecules; ds, double-stranded linear M13 DNA; ss, single-stranded circular M13 DNA.

Upon incubation of UL12 and ICP8 with the DNA substrates, joint molecules were formed (FIGS. 2 and 3, lanes 5–12). The simplest explanation for the slower migrating forms seen in FIG. 2 is that they represent joint molecules which result from a strand exchange reaction. Little or no slower migrating forms were observed when double stranded DNA was incubated alone with UL12 and ICP8 (data not shown). Incubation of ICP8 alone with the DNA substrates did not lead to formation of joint molecules, even after an 80 minute incubation (FIGS. 2 and 3, lane 2). Similarly, joint molecules were not observed with UL12. Incubation with UL12 alone merely led to the gradual degradation of the DNA substrates (FIGS. 2 and 3, lane 3 and data not shown). The reaction products demonstrated the same mobility whether they were loaded onto the gel using a buffer containing SDS (as in FIGS. 2–7) or whether they were treated with proteinase K prior to loading (data not shown). Therefore, the slowly migrating products were not the result of protein-DNA complexes with retarded mobility on agarose gels. When a loading buffer without SDS was used, most of the DNA failed to exit the well. This indicates that protein-DNA complexes formed during the assay are disrupted by the SDS loading buffer (data not shown).

Figure 4:
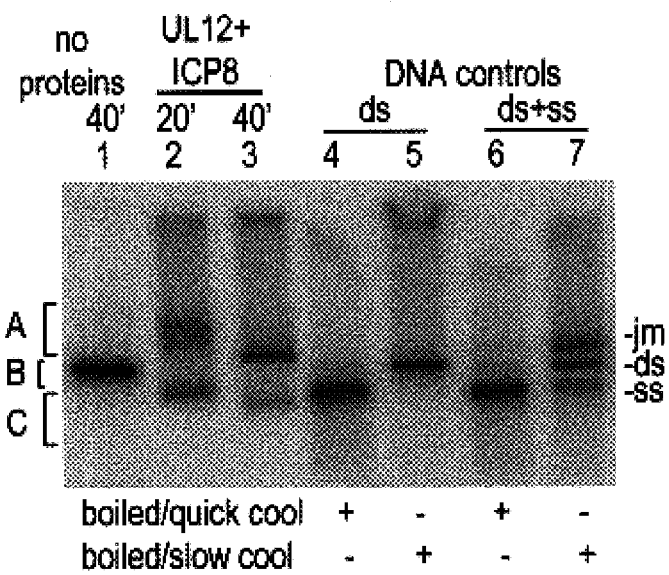
FIG. 4 shows an analysis of strand exchange products.

The progression of the strand exchange reaction over time is shown in FIGS. 2 and 3. During the reaction, two species of reaction products are produced: a slowly migrating species consisting of joint molecules, and a rapidly migrating species. The joint molecules produced are a heterogeneous population, probably including sigma, alpha, and possibly gapped circular forms, as shown in FIG. 1. The early joint molecule products migrate more slowly than those from later time points, reflecting the higher percentage of sigma forms with long tails assumed to be present at this stage. The expected products of a complete strand exchange reaction would be a gapped circle and a displaced linear single strand. In order to determine whether the expected gapped circles were produced, we compared the migration of the strand exchange products to the migration of known DNA controls In FIG. 4, the strand exchange products are compared to DNA controls. Strand exchange was performed using the [$^{32}$P]-labeled double-stranded DNA and unlabeled single-stranded DNA substrates. Lane 1 is a control reaction with no proteins added (40 minute incubation); lanes 2 and 3 are strand exchange with ICP8 and UL12 (20 and 40 minute time points, respectively). Lanes 4–7 represent various DNA-only controls. DNAs (double-stranded only in lanes 4–5, both double-stranded and single-stranded in lanes 6–7) were boiled for 2 min in strand exchange buffer and either quickly cooled on ice (lanes 4 and 6), or slowly cooled to allow strands to reanneal (lanes 5 and 7). Nicked circular, linear double-stranded, and linear single-stranded forms are produced when the two DNA substrates are boiled and allowed to reanneal slowly (FIG. 4, lane 7). The joint molecules produced after 40 minutes of incubation with ICP8 and UL12 (FIG. 4, lane 3) migrate similarly to the nicked circle (jm) seen in lane 7, suggesting that some strand exchange reactions have gone to completion. The expected products of a complete strand exchange reaction would be a gapped circle and a displaced linear single strand.

The second expected product of a complete strand exchange reaction is a displaced single strand. The displaced single strand should migrate rapidly, and therefore the rapidly migrating strand exchange products were investigated to see if such a displaced strand could be detected. At early time points (FIG. 2, lanes 5–7, and FIG. 4, lane 2), the fast-migrating band is found at a position between the original double-stranded substrate and the single-stranded DNA. Therefore, it appears to represent linear double-stranded DNA that has been shortened by the UL12 nuclease. At later time points, the fast-migrating species is found at the same position as the single-stranded DNA (FIG. 2, lanes 8–12, and FIG. 4, lane 3). This band could represent double-stranded DNA that was shortened further, or single-stranded DNA that was displaced during strand exchange.

Figure 5:
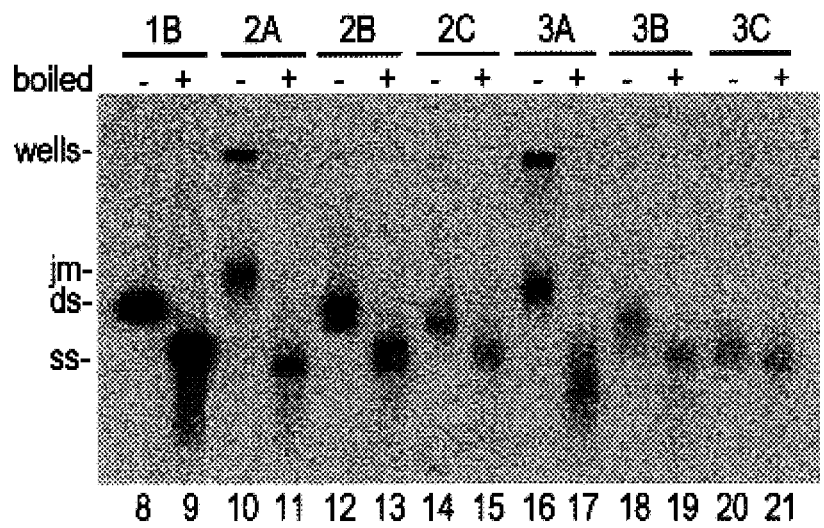
FIG. 5 shows another analysis of the strand exchange reaction.

In order to investigate these possibilities, the dsDNA substrate and products of the strand exchange reaction were isolated. The results are shown in FIG. 5. Strand exchange reactions were performed as in the experiment shown in FIG. 4, but were electrophoresed on a 1% low-melt agarose gel. Three gel slices were cut from each lane: A, containing joint molecules; B, containing remaining ds substrate; and C, containing low molecular weight products. The positions of A, B, and C gel slices are indicated in FIG. 5. The gel slices were melted at 65° C. and divided into two portions. One portion was loaded directly into the well of a second 1% agarose gel. The other portion was boiled for 2 minutes prior to loading. Electrophoresis was performed as for the strand exchange assay. Jm, joint molecules; ds, double-stranded DNA; ss, single-stranded DNA. This procedure was effective at separating the strands, as shown by the migration of the double-stranded DNA substrate (1B) with and without boiling (FIG. 5, lanes 8–9). The DNA strands of the various reaction products were also separated by boiling. Boiling of the joint molecule products (2A and 3A) released the strands that were paired with the circular ssDNA (FIG. 5, lanes 11 and 17). We can see that the pairing strands are shortened over time (compare lanes 11 to 17), most likely due to UL12 digestion. Interestingly, when the joint molecule products (FIG. 5, lanes 10 and 16) were run on the gel, a portion of the DNA did not exit the well. It is presumed that this is because when the gel slices were melted at 65° C., the DNA strands of the joint molecules were able to "breathe", allowing for reannealing between joint molecule species creating a complex which was unable to enter the gel. This complex was disrupted by boiling, as no DNA is evident in the wells when the joint molecules were boiled (FIG. 5, lanes 11 and 17). This experiment also demonstrates that the rapidly-migrating species (2C) from the 20 min reaction is double-stranded, as the migration pattern changes after boiling (FIG. 5, lanes 14–15). This fragment is most likely made up of double-stranded substrate molecules that were shortened by UL12. In contrast, the rapidly-migrating species (3C) from the 40 minutes reaction appears to be single-stranded, since its migration is unchanged by boiling (FIG. 5, lanes 20–21). We thus believe that this rapidly-migrating species is the displaced single strand. This result suggests that after 40 minutes of incubation, some of the strand exchange reactions have gone to completion, forming a gapped circular molecule and a displaced single strand.

Example 3

Validation of Identity of Displaced Strand

Figure 6:
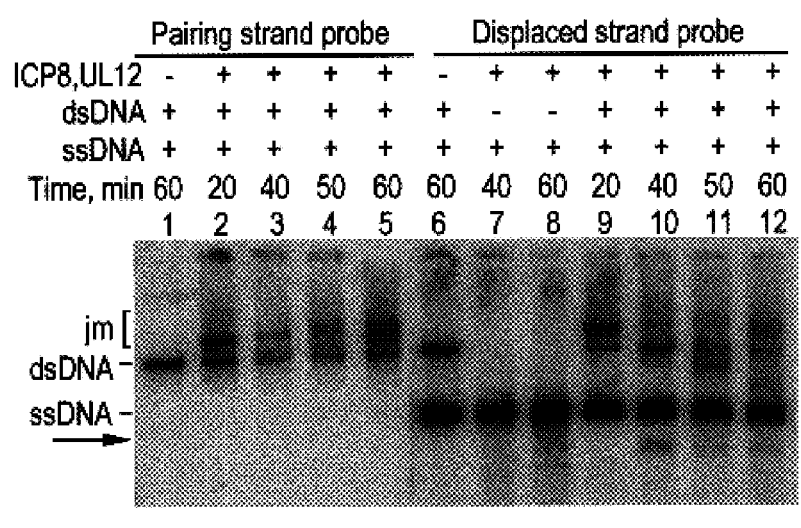
FIG. 6 shows a Southern blot of strand exchange reactions.

To further validate the identity of the displaced strand, the strand exchange reaction was analyzed by using a Southern blot (FIG. 6). Strand exchange assays were performed and loaded onto 1% agarose gels. Following electrophoresis, the DNA was blotted onto GeneScreen Plus membranes (Dupont) according to the manufacturer's suggested protocols. The oligonucleotide probes used to detect the M13 DNA strands were end-labeled with T4 polynucleotide kinase and [γ-$^{32}$P] ATP, using the "forward" reaction buffer supplied by the manufacturer (Life Technologies). The sequences of the two probes are as follows: SEQ ID NO:5 5'GTCGGT-GACGGTGATAATTCACCTTTAATG, for detection of the pairing, or "minus" strand; and SEQ ID NO:6 5'CAT-TAAAGGTGAATTATCACCGTCACCGAC, for detection of the displaced, or "plus" strand.

Reactions were performed using unlabeled substrates, and duplicate samples originating from the same tubes (with the exception of lanes 7–8), were loaded on a single agarose gel. The two halves of the membrane were probed with [$^{32}$P]-end labeled oligonucleotide probes, corresponding to nucleotides 2616–2645 of M13mp18, a position that is equidistant from the two ends of the PstI-cut M13 dsDNA. The left side of the membrane (FIG. 6, lanes 1–5) was probed with the oligonucleotide probe recognizing the pairing (minus) strand, while the right side (FIG. 6, lanes 6–12) was probed with the oligonucleotide recognizing the single-stranded M13 circular DNA and the displaced strand (plus strand). Both probes hybridized with the slowly-migrating strand exchange products. The rapidly migrating species seen after 40 minutes of incubation was only recognized by the "displaced strand" probe (FIG. 6, marked with an arrow). Therefore, this species is not likely to be a double-stranded DNA fragment shortened by UL12 action, because then both probes should have recognized it. Furthermore, the putative displaced strand does not appear to be degraded single-stranded DNA substrate, because similar bands are not seen when UL12 and ICP8 are incubated with the single-stranded substrate alone (FIG. 6, lanes 7–8). The displaced strand is less intense in the 50 and 60 minute time points (FIG. 6, lanes 11–12) presumably due to degradation by UL12. Taken together, these data indicate that UL12 and ICP8 mediate a true strand exchange reaction, one that includes both annealing and displacement.

Example 4

Conditions for Strand Exchange and UL12 Nuclease Activity

Figure 7:
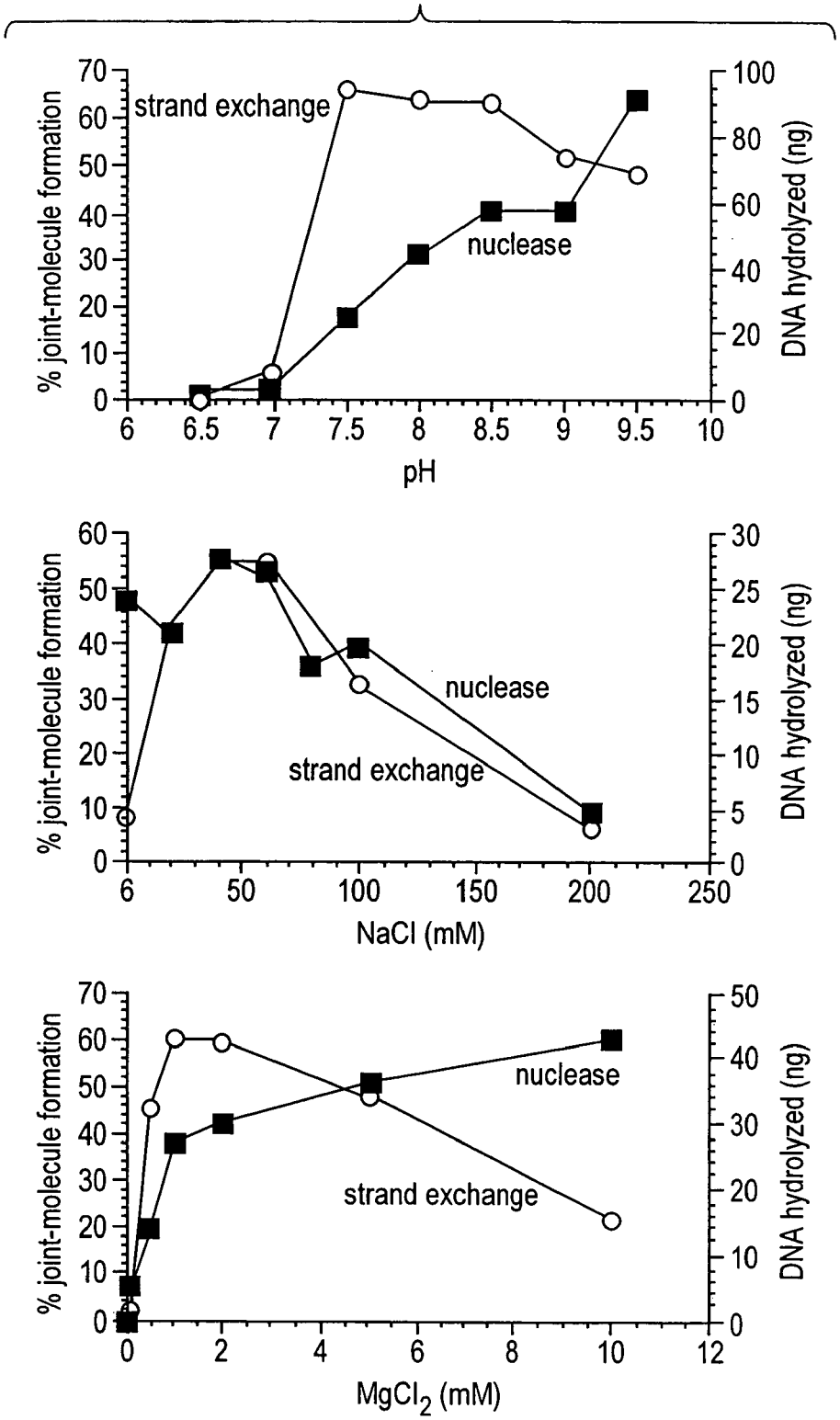
FIG. 7 shows strand exchange and UL12 nuclease activity at different conditions of concentration of $Mg^{2+}$, concentration of $Na^+$, and pH.

Strand exchange by UL12/ICP8 and UL12 nuclease activity were assayed under different conditions of pH, Na$^+$, and Mg$^{2+}$ concentration, and the results are presented in FIG. 7. Nuclease activity was measured as follows. Total unlabeled chromosomal DNA from E. coli was isolated from late log-phase UT481 cells by phenol extraction and ethanol precipitation essentially. [Thymidine-methyl-3H]-DNA (E. coli) was mixed with unlabeled chromosomal E. coli DNA to provide a substrate with the desired specific radioactivity. The nuclease assay was performed in a 50 microliters volume, with 250 nanograms [$^3$H]-DNA as the substrate. UL12 (47 nanograms, 13.9 nM) and ICP8 (11.25 micrograms, 1.75 µM) were assayed for nuclease using the same concentrations of these proteins and the same assay buffer as were used in the strand exchange assay. Reactions were incubated 10 minutes at 37° C., then stopped with 150 microliters of 0.5% yeast RNA and 200 microliters of 20% (wt/vol) trichloroacetic acid. After 10 minutes on ice, samples were centrifuged for 10 minutes at 14,000×g, and radioactivity in 200 microliters of the supernatant fraction was determined by scintillation counting. Results presented are averages of duplicate determinations.

The extent of strand exchange was determined by measuring the amount of DNA that had migrated as a high molecular weight species at 20 minutes of incubation. In FIG. 7, open circles show strand exchange; closed squares show nuclease activity. Unless indicated otherwise, the conditions were pH 7.5, 1 mM MgCl$_2$, and 40 mM NaCl. Strand exchange assays were incubated for 20 minutes. Percent strand exchange was calculated as the percentage of radioactivity in joint-molecule products out of the total radioactivity in the lane. Nuclease activity of UL12 was assayed using the [$^3$H]-E. coli DNA substrate and is represented as the amount of DNA (in nanograms) digested by 47 nanograms UL12 (13.9 nM) in a 10 minute assay at 37° C. The results show a correlation of high strand exchange activity with moderate UL12 nuclease activity. The UL12 nuclease, also known as the alkaline nuclease, exhibits a pH optimum of 9–10. Strand exchange activity was highest at pH 7.5–8.5, a pH range that supported an intermediate amount of UL12 nuclease activity. At pH levels below 7.5, both the nuclease and strand exchange activities were abrogated. This was not a buffer effect, as nuclease activity and strand exchange were the same whether Hepes or Tris buffers were used at pH 7.5 (data not shown). At high NaCl concentrations, both UL12 nuclease activity and strand exchange were inhibited. In contrast, although UL12 nuclease was active in the absence of NaCl, strand exchange was not observed in the absence of NaCl. UL12 nuclease activity is optimal at higher magnesium concentrations. However, at these concentrations, more of the double-stranded substrate was degraded than exchanged (FIG. 6 and data not shown). In the absence of magnesium, UL12 nuclease was inactive, and strand exchange did not occur. Optimal strand exchange was achieved at low magnesium concentrations, which allowed for a moderate amount of UL12 nuclease activity. Low magnesium concentrations also promote branch migration, which would be expected to potentiate strand exchange. The optimal conditions for strand exchange were intermediate between the optima for strand melting and strand annealing by ICP8. For true strand exchange to occur, ICP8 must be able to mediate both strand melting and strand annealing. The ICP8 annealing activity is optimal at 6mM $MgCl_2$ and 80 mM NaCl, and is significantly reduced at low levels of $MgCl_2$ and NaCl. In contrast, the ICP8 helix destabilizing activity is highest at low $MgCl_2$ levels (0–1 mM) and in the total absence of salt. Both strand-melting and strand-annealing activities of ICP8 are functional at pH 7–9. Thus, the conditions found to be optimal for strand exchange were those that allowed for moderate levels of all three activities involved in this reaction: nuclease, strand melting, and strand annealing.

In other experiments, the ability of either manganese or zinc to replace magnesium in the strand exchange assay was tested. Manganese could support some strand exchange, but zinc could not (data not shown). This is consistent with previous reports on the effect of divalent cations on UL12 activity. In addition, ATP was not required for strand exchange, nor did it enhance the activity (data not shown).

The double stranded fragment in the standard strand exchange assay was cut with PstI, which leaves four-base 3' overhangs. In order to test whether the nature of the double-stranded end was important in the reaction, double-stranded substrates that had been cut with SmaI, which leaves blunt ends, and BamHI, which leaves four base 5' overhangs were used. Since all three sites are clustered in the polylinker region of M13mp18, any differences between them should be attributable to the nature of the end, and not to local sequence context. No differences were noted in the ability of UL12/ICP8 to promote strand exchange using substrates with the different types of overhanging ends (data not shown). In order to make the assay more sensitive, a competition experiment was used. The strand exchange assay was performed using a mixture of [$^{32}$P]-labeled PstI-cut dsDNA (50 nanograms) and unlabeled dsDNA (125 nanograms), cut with either PstI, BamHI, or SmaI. If the new substrates are utilized either more or less efficiently than the PstI cut substrate, a change in the amount of labeled PstI substrate that undergoes strand exchange would be expected. Neither of the new substrates caused a change, suggesting that the three substrates were utilized equally (data not shown).

Figure 8:
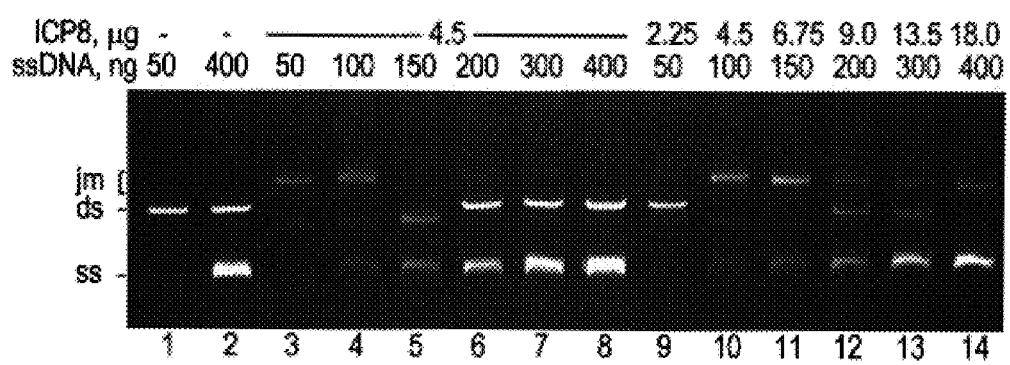
FIG. 8 shows a titration of single-stranded DNA and ICP8 in the strand exchange assay.

For complete coverage of the 100 nanograms of single-stranded M13 DNA used in the strand exchange assay, 3.7 micrograms of ICP8 are required (15, 40). The assays were done with a slight excess (4.5 micrograms) over this minimal amount. FIG. 8 shows a titration of single-stranded DNA and ICP8 in the strand exchange reaction. Strand exchange reactions were performed with 20 minute incubations. UL12 and double-stranded DNA were added according to standard conditions, while the amounts of single-stranded DNA and ICP8 used are indicated in the figure. A photograph of the ethidium bromide-stained gel is shown. Lanes 1–2 are no protein controls. Jm, joint molecules; ds, double-stranded DNA; ss, single-stranded DNA. When increasing amounts of single-stranded DNA were added to the strand exchange assay, such that the amount of ICP8 was insufficient for full coverage, strand exchange was reduced accordingly (FIG. 8, lanes 6–8). When the amount of ICP8 was increased to correlate with the increases in single stranded DNA (FIG. 8, lanes 9–14), strand exchange was restored. Therefore, efficient strand exchange appeared to require stoichiometric amounts of ICP8. This experiment also demonstrates that moderate excess of ICP8 does not inhibit strand exchange (FIG. 8, lane 3).

Example 5

Active UL12 is Required for Strand Exchange

Figure 9:
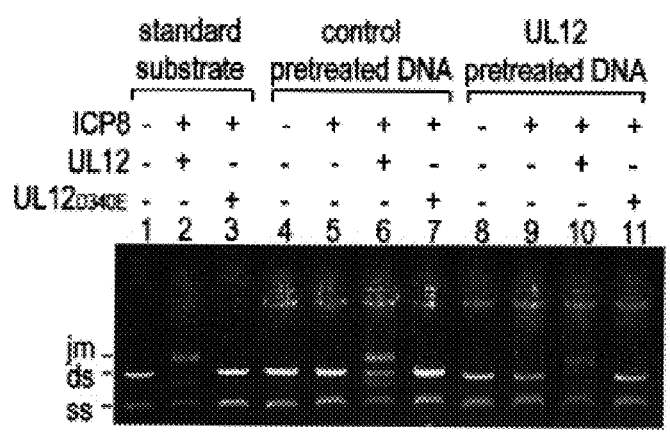
FIG. 9 shows strand exchange by UL12, $UL12_{D340E}$, and ICP8 using standard and preresected double stranded substrates. A photograph of the ethidium bromide-stained gel is shown.

A mutant UL12 protein, $UL12_{D340E}$, was previously purified and characterized (Goldstein, J. N. and Weller, S. W. (1998) *Virology* 244: 442–57). This protein has a single point mutation that has eliminated its exonuclease activity. The experiment is shown in FIG. 9. In lanes 1–3, strand exchange was carried out with 4.5 micrograms ICP8, 18.8 nanograms UL12, and 20 nanograms $UL12_{D340E}$, as indicated. Reactions were incubated for 20 minutes at 37° C. In lanes 4–11, strand exchange was performed using pretreated double-stranded substrates. The pretreated substrates were prepared as follows: the PstI-cut M13 dsDNA substrate was incubated in strand exchange buffer for 20 minutes at 37° C. either with or without UL12, under strand exchange conditions (18.8 nanograms UL12 per 100 nanograms dsDNA). The reaction was heat-inactivated 10 minutes at 65° C., and the DNA was phenol/chloroform extracted and ethanol precipitated. This pretreated DNA was then used in a standard strand exchange assay, with the amounts of protein as indicated above. Reactions were incubated for 20 minutes at 37° C.

When included in the strand exchange assay, the mutant protein was unable to promote strand exchange (FIG. 9, lane 3), both at the standard UL12 concentration (FIG. 9) and when present at ten times the standard concentration (data not shown). This deficiency cannot be attributable to a global effect of the mutation on UL12, as the mutant protein still retains certain activities. Excess mutant protein was able to inhibit wild-type UL12, both in the strand exchange assay, and in the nuclease assay (data not shown). The mechanism of inhibition is probably through competition for the DNA substrate, as the inhibition of the nuclease activity was seen only at low substrate DNA concentrations (data not shown).

The model for strand exchange outlined in FIG. 1 proposes that the first step involves the digestion of the double-stranded DNA by UL12, revealing a 3' single-stranded DNA tail that is later annealed by ICP8 to the circular single stranded DNA. This model predicts that the two events could be separated and yet still lead to strand exchange. Specifically, it suggests that ICP8 could mediate strand exchange of DNA that had been preresected by UL12. In order to test this possibility, DNA was incubated with or without UL12 for 20 minutes under standard assay conditions. The treated DNA was re-purified, and subjected to strand exchange. Nuclease S1 analysis of the preresected substrates indicated that UL12 had removed approximately 2000 bases (data not shown). FIG. 9 shows that even when the double-stranded DNA was preresected by UL12, strand exchange occurred only when both UL12 and ICP8 were present together. ICP8 alone could not effect strand exchange (lane 9), and mutant UL12 could not substitute for wild-type UL12, even with preresected DNA (lane 11). This was tested at both high and low concentrations of the mutant protein (FIG. 9 and data not shown). Together, these data indicate that strand exchange mediated by ICP8 requires the presence and activity of the UL12 nuclease.

The data presented demonstrate that the HSV-1 alkaline nuclease (UL12) and single-strand DNA binding polypeptide (ICP8) work together to carry out a strand exchange reaction. This reaction requires both proteins for strand exchange to occur. The activities shown here for UL12/ICP8 suggest that it may be a member of the family of two component viral recombinases comprised of an alkaline exonuclease and an associated single-stranded DNA annealing protein. This family of proteins can mediate strand exchange in the absence of a high-energy cofactor.

With regard to HSV-1, recombination occurring during replication of HSV-1 DNA could be of several types. A strand-annealing mechanism could be used by the virus to generate genomic concatemers. Since the HSV-1 genome has direct repeats at its ends, concatemerization through single-strand annealing could proceed through a mechanism similar to that used by bacteriophage lambda. UL12/ICP8 could potentially be the mediator of such a mechanism. Another intriguing possibility is that strand invasion could be used by HSV-1 to prime DNA replication. Alternatively, because the HSV-1 DNA contains numerous gaps, it is possible that DNA replication could be primed by an invading strand annealing to a single-stranded gapped region without requiring true "invasion". The HSV-1 helicase-primase complex was shown to participate with ICP8 in mediating a strand exchange reaction that uses resected substrates. The ability of the HSV-1 proteins UL12, ICP8 and the helicase-primase to participate in strand transfer reactions is interesting in light of the tight linkage between DNA replication and recombination in this virus.

The HSV recombinase is particularly useful in methods of homologous recombination in eukaryotic systems, particularly in cases where the size of the polynucleotide is large (e.g., a mammalian gene, for example). The HSV recombinase can be used in methods of performing homologous recombination between a donor polynucleotide and a target polynucleotide. The HSV recombinase can be part of a cloning kit, for example. Such cloning kits are particularly useful when the donor polynucleotide comprises a human gene. Other methods include methods of treating host cells and methods of treating an organism in, for example, gene therapy applications. The HSV recombinase can also be used to make transgenic non-human animals. The HSV recombinase can also be used in methods of modifying host cells. Because the HSV recombinase is from a virus that infects eukaryotes, the recombinase should be more efficient in recombination involving mammalian genes than the previously studied bacterial recombinases. In addition, the ability of the HSV recombinase to participate in homologous recombination instead of site-specific recombination allows targeting to virtually any desired DNA sequence.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated herein by reference in their entirety.

The invention claimed is:

1. A purified or isolated Herpes simplex virus recombinase comprising an alkaline nuclease comprising an amino acid sequence which is at least 95% identical to a Herpes simplex virus-1 UL12 alkaline nuclease of SEQ ID NO: 2 and a single stranded DNA binding polypeptide comprising an amino acid sequence which is at least 95% identical to a Herpes simplex virus-1 ICP8 single stranded DNA binding polypeptide of SEQ ID NO: 4, and wherein the recombinase has polynucleotide strand exchange activity.

2. The purified or isolated Herpes simplex virus recombinase of claim 1, comprising SEQ ID NO: 2 and SEQ ID NO: 4.

3. The purified or isolated Herpes simplex virus recombinase of claim 2, wherein the ratio of the alkaline nuclease to the single stranded DNA binding polypeptide is 1:500 to 1:1.

4. The purified or isolated Herpes simplex virus recombinase of claim 1, wherein the alkaline nuclease, the single stranded DNA binding polypeptide, or both are isolated polypeptides.

5. The purified or isolated Herpes simplex virus recombinase of claim 1, wherein the alkaline nuclease, the single stranded DNA binding polypeptide, or both are purified polypeptides.

6. The purified or isolated Herpes simplex virus recombinase of claim 1, wherein the alkaline nuclease, the single stranded DNA binding polypeptide, or both are expressed in a host cell.

7. The purified or isolated Herpes simplex virus recombinase of claim 6, wherein the host cell is an insect cell or a VERO cell.

8. A method of promoting homologous recombination, comprising contacting:

a purified or isolated Herpes simplex virus recombinase, wherein the Herpes simplex virus recombinase comprises an alkaline nuclease comprising an amino acid sequence which is at least 95% identical to a Herpes simplex virus-1 UL12 alkaline nuclease of SEQ ID NO: 2 and a single stranded DNA binding polypeptide, comprising an amino acid sequence which is at least 95% identical to a Herpes simplex virus-1 ICP8 single stranded DNA binding polypeptide of SEQ ID NO: 4, and wherein the recombinase has polynucleotide strand exchange activity;

a donor polynucleotide comprising a first donor homology region at a first end, a second donor homology region at a second end, and an exogenous sequence therebetween; and a target polynucleotide comprising a first target homology region at a first end, a second target homology region at a second end, and an endogenous sequence therebetween;

wherein contacting is performed under conditions sufficient to promote homologous recombination.

9. The method of claim 8, wherein the first donor homology region and the first target homology region are substantially homologous; and wherein the second donor homology region and the second target homology region are substantially homologous.

10. The method of claim 8, wherein contacting is in vitro.

11. The method of claim 10, wherein the alkaline nuclease comprises purified Herpes simplex virus-1 UL12 and the single stranded DNA binding polypeptide comprises purified Herpes simplex virus-1 ICP8.

12. The method of claim 8, wherein contacting is in a host cell.

13. The method of claim 12, wherein the host cell is a mammalian cell.

14. The method of claim 12, wherein the host cell comprises a first polynucleotide comprising a Herpes simplex virus-1 UL12 polynucleotide operatively linked to expression control sequences, and a second polynucleotide comprising a Herpes simplex virus-1 ICP8 polynucleotide operatively linked to expression control sequences.

15. A cloning kit, comprising:
a Herpes simplex virus recombinase, wherein the Herpes simplex virus recombinase comprises an alkaline nuclease comprising an amino acid sequence which is at least 95% identical to a Herpes simplex virus-1 UL12 alkaline nuclease of SEQ ID NO: 2 and a single stranded DNA binding polypeptide, comprising an amino acid sequence which is at least 95% identical to a Herpes simplex virus-1 ICP8 single stranded DNA binding polypeptide of SEQ ID NO: 4, and wherein the recombinase has polynucleotide strand exchange activity; and
a target polynucleotide comprising a first target homology region at a first end, a second target homology region at a second end, and an endogenous sequence therebetween.

16. The cloning kit of claim 15, wherein the Herpes simplex virus recombinase comprises SEQ ID NO: 2 and SEQ ID NO: 4.

17. The cloning kit of claim 15, further comprising a host cell.

18. The cloning kit of claim 17, wherein the host cell comprises a first polynucleotide comprising a nucleotide sequence which is at least 95% homologous to a Herpes simplex virus-1 UL12 polynucleotide of SEQ ID NO: 1, operatively linked to expression control sequences, and a second polynucleotide comprising a nucleotide sequence which is at least 95% homologous to a Herpes simplex virus-1 ICP8 polynucleotide of SEQ ID NO: 3, operatively linked to expression control sequences.

19. The cloning kit of claim 15, wherein the endogenous sequence comprises a polylinker.

20. The cloning kit of claim 15 wherein the endogenous sequence comprises at least one regulatory sequence for protein expression.

21. A method of making a modified host cell comprising:
delivering to the host cell a composition comprising a Herpes simplex virus recombinase; and a donor polynucleotide comprising a first donor homology region at a first end, a second donor homology region at a second end, and an exogenous sequence therebetween; wherein the Herpes simplex virus recombinase comprises an alkaline nuclease comprising an amino acid sequence which is at least 95% identical to a Herpes simplex virus-1 UL12 alkaline nuclease of SEQ ID NO: 2 and a single stranded DNA binding polypeptide comprising an amino acid sequence which is at least 95% identical to a Herpes simplex virus-1 ICP8 single stranded DNA binding polypeptide of SEQ ID NO: 4, and wherein the recombinase has polynucleotide strand exchange activity.

22. The method of claim 21, wherein the Herpes simplex virus recombinase comprises SEQ ID NO: 2 and SEQ ID NO: 4.

* * * * *